United States Patent
Ramana et al.

(10) Patent No.: US 10,774,060 B2
(45) Date of Patent: Sep. 15, 2020

(54) OXONE-ACETON MEDIATED METAL FREE PREPARATION OF SYN-DIOLS

(71) Applicant: Council of Scientific & Industrial Research, New Dehli (IN)

(72) Inventors: Chepuri Venkata Ramana, Pune (IN); Ravindra Suresh Phatake, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 357 days.

(21) Appl. No.: 14/392,212

(22) PCT Filed: Jun. 25, 2014

(86) PCT No.: PCT/IN2014/000425
§ 371 (c)(1),
(2) Date: Dec. 23, 2015

(87) PCT Pub. No.: WO2014/207766
PCT Pub. Date: Dec. 31, 2014

(65) Prior Publication Data
US 2016/0168114 A1    Jun. 16, 2016

(30) Foreign Application Priority Data

Jun. 25, 2013 (IN) .......................... 1873/DEL/2013

(51) Int. Cl.
| | | |
|---|---|---|
| *C07D 317/70* | (2006.01) | |
| *C07C 245/24* | (2006.01) | |
| *C07C 45/40* | (2006.01) | |
| *C07D 493/04* | (2006.01) | |
| *C07D 317/12* | (2006.01) | |
| *C07C 49/67* | (2006.01) | |
| *C07C 49/784* | (2006.01) | |
| *C07C 49/755* | (2006.01) | |
| *C07C 49/697* | (2006.01) | |
| *C07C 45/27* | (2006.01) | |

(52) U.S. Cl.
CPC ............ *C07D 317/70* (2013.01); *C07C 45/27* (2013.01); *C07C 45/40* (2013.01); *C07C 49/67* (2013.01); *C07C 49/697* (2013.01); *C07C 49/755* (2013.01); *C07C 49/784* (2013.01); *C07D 317/12* (2013.01); *C07D 493/04* (2013.01); *C07C 2602/06* (2017.05); *C07C 2602/10* (2017.05)

(58) Field of Classification Search
None
See application file for complete search history.

(56) References Cited

FOREIGN PATENT DOCUMENTS

CN    101 497 608 B    11/2011

OTHER PUBLICATIONS

Rawling et a., Metal-free syn-dioxygenation of alkenes. Organic & Biomolecular Chemistry, 2013, 11, 1434-1440.*
Banwell, Martin G. et al.: "A Total Synthesis of the Styryllactone (+)-Goniodiol from Naphthalene"; AU J. Chem., Jun. 11, 2003, vol. 56, pp. 585-595.
Burgstahler, Albert W. et al.: "The Synthesis of o-Di-t-butylbenzene by Classical Reaction Methods1"; J. Am. Chem. Society, vol. 85, No. 2, Jan. 1, 1963, pp. 173-180.
Desjardins, Michel et al.: "Synthesis and biological evaluation of conduritol and conduramine analogs", J. Chem Society, Perkin Transactions vol. 1, No. 5, Jan. 1, 1999, pp. 621-628.
Kim, Sunggak et al.: "Synthesis of conjugated dienes from vinyl epoxides, vinyl acetonides and 2,5-dihydrofurans via zirconocene-mediated deoxygenation"; J. Chem Society, Perkin Transactions vol. 1, No. 8, Jan. 1, 1997, pp. 1095-1098.
Lo, Ching-Yu et al.: "Efficient Synthesis of Functionalized Furans via Ruthenium-Catalyzed Cyclization of Epoxyalkyne Derivatives—Supporting Informations", J. Organic Chem., Jan. 1, 2002, pp. 1-40.
Mukherjee, Parag et al.: "A Diversity-Oriented Synthesis of Bicyclic cis-Dihydroarenediols, cis-4-Hydroxyscytalones, and Bicyclic Conduritol Analogues", Organic Letters, vol. 12, No. 11, Jun. 4, 2010, pp. 2472-2475.
Orsini, F. et al: "Chemoenzymatic synthesis of conduritol analogues", Tetrahedron Letters, Pergamon, GB, vol. 45, No. 50, Dec. 6, 2004, pp. 9253-9255.

(Continued)

*Primary Examiner* — Po-Chih Chen
(74) *Attorney, Agent, or Firm* — Dinsmore & Shohl, LLP

(57) ABSTRACT

The present invention disclose a simple and high yielding process of Oxone-acetone mediated metal free syn-dihydroxylation of benzo fused olefins of formula (II) to obtain library of dioxolo compounds of formula (I). The invention further disclose a simple and high yielding process of Oxone-acetone mediated metal free syn-dihydroxylation of stilbene and its derivatives of formula (III) thereof. Also disclosed herein is Wacker-type oxidation of benzo-fused olefins of formula (X). The invention further disclose compounds of formula (I) which can be useful for the treatment of HIV, cancer or malaria.

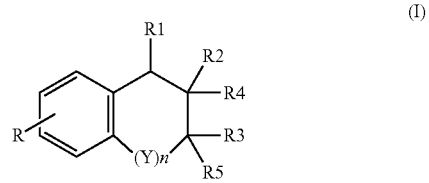

10 Claims, No Drawings

(56) References Cited

OTHER PUBLICATIONS

Orsini, F. et al.: "*Cyclic Chiral Diols with C2 Symmetry: Synthesis of (2R, 3R)-dihydroxy-1,2,3,4-Tetrahydronaphthalene*", Tetrahedron Asymmetry, Pergamon Press Ltd, Oxford, GB, vol. 7, No. 4, Apr. 1, 1996, pp. 1033-1040.
Salem, Bahaâ et al.: "*Cyclocarbopalladation:? 5-Exo-dig Cyclization versus Direct Stille Cross-Coupling Reaction. The Influence of the [alpha],[beta]-Propargylic Substitution*", Organic Letters, vol. 5, No. 13, Jun. 1, 2003, pp. 2307-2310.
Tsang, Wing Sum et al.: "*Chemistry of anti- and syn-1,2:3,4-naphthalene dioxides and their potential relevance as metabolic intermediates*", J. Organic Chem, Am Chem Society, vol. 47, No. 27, Dec. 1, 1982, pp. 5339-5353.
International Search Report dated Feb. 5, 2015, regarding PCT/IN2015/000425.

\* cited by examiner

OXONE-ACETON MEDIATED METAL FREE PREPARATION OF SYN-DIOLS

CROSS-REFERENCE TO RELATED APPLICATIONS

This application is a 35 USC § 371 National Stage application of International Application No. PCT/IN2014/000425 filed Jun. 25, 2014, now pending; which claims the benefit under 35 USC § 119(a) to India Application No. 1873/DEL/2013 filed Jun. 25, 2013.

FIELD OF THE INVENTION

The present invention relates to a simple and high yielding process of Oxone-acetone mediated metal free syn-dihydroxylation of benzo fused olefins of formula (II) to obtain library of dioxolo compounds of formula (I). Particularly, the invention further relates to a simple and high yielding process of Oxone-acetone mediated metal free syn-dihydroxylation of stilbene and its derivatives of formula (III). More particularly, the present invention also relates to Wacker-type oxidation of benzo-fused olefins of formula (X).

BACKGROUND OF THE INVENTION

The Oxone-mediated syn-dihydroxylation is a significant step in the area of metal-free dihydroxylations in general and for the synthesis of the indene acetonides in particular. Previous reports on the synthesis of these compounds are multistep in nature and employing explosive reagents such as peroxides for epoxidation, and strong acid treatment for the epoxide opening and then protection of the resulting diol as acetonide. Regioselectivity during the epoxide opening is one of the biggest problems till date.

The 1,2-diol unit is one of the most ubiquitous moiety in the natural products, pharmaceuticals and arguably has attracted significant amount of synthetic maneuvers since the beginning. The syn-/anti-dihydroxylation of alkenes has been considered as a simple approach for the installation of these 1,2-diol units, which in general has been mainly reserved for the metal-based reagents. The $OsO_4$, introduced by Criegee, is the most commonly employed catalyst for the syn-dihydroxylation of olefins and was central to many developments in this area. The toxicity of osmium taken together with its volatility has led to explore the several other metals for this purpose; however, in general the metal-based syn-dihydroxylations have limitations in terms of the waste generated and also because of the difficulties in complete removal of the metal impurities from the products. Thus the metal free method for the dihydroxylation of alkenes is the most desired alternative and renewed interest being shown in the recent years. The phthaloyl peroxide (PPO), is the first reagent that has been employed for the metal free direct dihydroxylations by Greene. Though the reaction is stereospecific and documented as early as in 1956, the problems associated with instability/explosive nature of the reagent and the poor product yields have been dealt only recently by introducing cyclic acyl peroxides by Tomkinson and co workers. The closely related more reactive cyclic peroxides, the dioxiranes, have been widely employed for the epoxidations. The one-pot combination of olefin epoxidation and subsequent opening leading to vicinal diols has been also well established with the dioxiranes, however, it results either in trans-dihydroxylation products or diastereomeric mixture depending upon the conditions.

The direct dihydroxylations with dioxiranes are rare. In 2000, White and co-workers, later in 2008 De Kimpe and co-workers reported the syn-dihydroxylation as a side reaction during the synthesis of patulin and mollugin. The corresponding acetonides have been isolated along with the expected epoxides. In both the instances, the scope of the reaction has been limited to specific substrates. These are unexpected and important findings and yet the potential of this syn-dihydroxylation with Oxone-acetone combination has been not yet tapped.

OBJECTS OF THE INVENTION

The main object of the present invention is to provide a process for the preparation of syn-diol of formula I of benzo-fused cyclic olefins of formula II.

Another object of the invention is to provide a process for the preparation of syn-diol of stilbene and its derivatives of formula (TV).

Yet another object of the present invention is to provide a process which is stereospecific and does not proceed via the epoxide route.

Yet another object of the present invention is to provide Wacker-type oxidation of benzo-fused cyclic olefins of formula (X).

SUMMARY OF THE INVENTION

Accordingly, present invention provides a simple, one step, stereospecific, oxone-acetone mediated, metal free propreparation of dioxolo compounds of benzo-fused cyclic olefins of Formula (I)

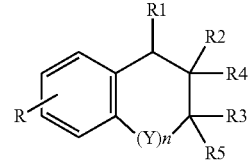

Formula I wherein;
R1 and R2, or R2 and R3, or R5 together with —CHR6 represent dioxolo

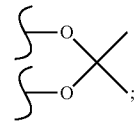

and
R1, or R2, or R3, or R4, or R5 which do not form the dioxolo group is are independently selected from the group consisting of hydrogen, alkoxy, (un)substituted or substituted phenyl, halogen, hydroxy, nitro, amino, carbonyl, —COOH, cyano, azo, (un)substituted or substituted benzyl group, C1 to C6 cyclo compounds optionally having one or more heteroatoms selected from N, O or S, heteroaryl, (un)substituted linear or branched alkyl radical having 1 to 10 C atoms, substituted linear or branched alkyl radical having 1 to 10 C atoms, in which one or more CH2 groups optionally each independently of one another be replaced by —C=O, —N—, —O—, —S—, —CH=CH—, or —C≡C—, (un)

substituted linear or branched alkenyl radical having 1 to 10 C atoms, substituted linear or branched alkenyl radical having 1 to 10 C atoms, (un)substituted linear or branched alkynyl radical having 1 to 10 C atoms, substituted linear or branched alkynyl radical having 1 to 10 C atoms;

'Y' is —CHR6, or heteroatom; wherein R6 is selected from hydrogen, methyl, and phenyl;

R is hydrogen or alkoxy;

'n' is 0 or 1; with the proviso when n=0; Formula I may form five membered ring or three carbon chain; when n=1 Formula I may form six member ring; said process comprising:

(i) mixing compound of Formula (II)

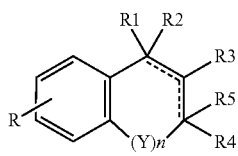
(II)

wherein;

R1 and R2, or R2 and R3, or R5 together with —CHR6 represent dioxolo

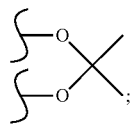
;

and

R1, or R2, or R3, or R4, or R5 are independently selected from the group consisting of hydrogen, alkoxy, (un)substituted or substituted phenyl, halogen, hydroxy, nitro, amino, carbonyl, —COOH, cyano, azo, (un)substituted or substituted benzyl group, C1 to C6 cyclo compounds which optionally having one or more heteroatoms selected from N, O or S, heteroaryl, (un)substituted linear or branched alkyl radical having 1 to 10 C atoms, substituted linear or branched alkyl radical having 1 to 10 C atoms, in which one or more CH2 groups optionally each independently of one another be replaced by —C=O, —N—, —O—, —S—, —CH=CH—, or —C≡C—, (un)substituted linear or branched alkenyl radical having 1 to 10 C atoms, substituted linear or branched alkenyl radical having 1 to 10 C atoms, (un)substituted linear or branched alkynyl radical having 1 to 10 C atoms, substituted linear or branched alkynyl radical having 1 to 10 C atoms;

'Y' is —CHR6, or heteroatom; wherein R6 is selected from hydrogen, methyl, and phenyl;

R is hydrogen or alkoxy;

'n' is 0 or 1; with the proviso when n=0; Formula I may form five membered ring or three carbon chain; when n=1 Formula I may form six member ring ······· represents a double or single bond;

with powdered Oxone (H3K5S4O18) and sodium bicarbonate (NaHCO3) in a ratio in the range of 2:3 in a mixture of solvents to obtain a reaction mixture;

(ii) stirring the reaction mixture obtained in step (i) at room temperature in the range of 25 to 30° C. for a period in the range of 2-5 hours; and (iii) evaporating excess acetone under reduced pressure on completion of reaction, portioning the remaining reaction mixture between water and ethyl acetate followed by purification to obtain compound of Formula I. In an another embodiment of the invention the solvents used in step (i) are acetone, ethyl acetate, and water in the ratio of 5:1:1.

In an another embodiment of the invention the structure formula of the dioxolo compounds of Formula I are selected from the group consisting of:

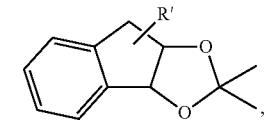
(VI)

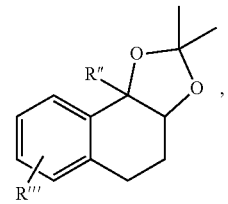
(VIII)

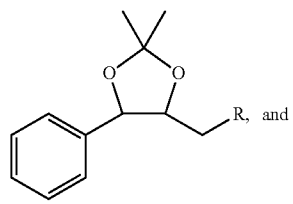
(IV)

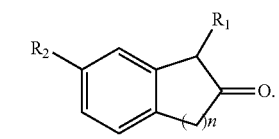
(X)

wherein R' and R" represent independently of each other groups selected from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl; a linear or branched alkyl radical having 1 to 10 C atoms which is (un)substituted or substituted; in which one or more CH2 groups may each, independently of one another, be replaced by —C=O, —N—, —O— or —S—, —CH=CH—, —C≡C—; a linear or branched alkenyl radical having 1 to 10 C atoms which is (un)substituted or substituted; a linear or branched alkynyl radical having 1 to 10C atoms which is (un)substituted or substituted.

R and R''' is selected from hydrogen or alkoxy.

R1 is selected independently of each other from the group consisting of hydrogen, alkyl or aryl;

R2 is hydrogen or alkoxy; and

'n' is 1 or 2.

In another embodiment of the invention the dioxolo compounds of Formula I are selected from the group consisting of:

(i) 2,2-dimethyl-8,8a-dihydro-3aH-indeno[1,2-d][1,3]dioxole (2a);
(ii) 2,2-dimethyl-3a-propyl-8,8a-dihydro-3aH-indeno[1,2-d][1,3]dioxole (2b);
(iii) 3a-(3-chloropropyl)-2,2-dimethyl-8,8a-dihydro-3aH-indeno[1,2-d][1,3]dioxole (2c);
(iv) 8-(4-bromobutyl)-2,2-dimethyl-8,8a-dihydro-3aH-indeno[1,2-d][1,3]dioxole (2d);
(v) 8-benzyl-2,2-dimethyl-8,8a-dihydro-3aH-indeno[1,2-d][1,3]dioxole (2e);
(vi) 3a-benzyl-2,2-dimethyl-8,8a-dihydro-3aH-indeno[1,2-d][1,3]dioxole (2f);
(vii) 3a-isopropyl-2,2-dimethyl-8,8a-dihydro-3aH-indeno[1,2-d][1,3]dioxole (2g);
(viii) 3a-cyclohexyl-2,2-dimethyl-8,8a-dihydro-3aH-indeno[2,1-d][1,3]dioxole (2h);
(ix) 2,2-dimethyl-3a-phenyl-8,8a-dihydro-3aH-indeno[1,2-d][1,3]dioxole (2i);
(x) 7-(2,2-dimethyl-8,8a-dihydro-3aH-indeno[2,1-d][1,3]dioxol-3a-yl)heptan-2-one (2j);
(xi) 2',2'-dimethyl-3a',8a'-dihydrospiro[cyclopentane-1,8'-indeno[2,1-d][1,3]dioxole] (2k);
(xii) 3a-(but-3-enyl)-2,2-dimethyl-8,8a-dihydro-3aH-indeno[2,1-d][1,3]dioxole (2m);
(xiii) 2,2,9b-Trimethyl-3a,4,5,9b-tetrahydronaphtho[2,1-d][1,3]dioxole (2o);
(xiv) 7-Methoxy-2,2,9b-trimethyl-3a,4,5,9b-tetrahydronaphtho[1,2-d][1,3]dioxole (2p);
(xv) 2,2-Dimethyl-9b-phenyl-3a,4,5,9btetrahydronaphtho[2,1-d][1,3]dioxole (2q);
(xvi) 7-Methoxy-2,2-dimethyl-9b-phenyl-3a,4,5,9b-tetrahydronaphtho[1,2-d][1,3]dioxole (2r); and
(xvii) 2,2-dimethyl-3a-(2-(oxiran-2-yl)ethyl)-3a, 8a-dihydro-8H indeno[1,2-d][1,3]dioxole (6).
(xviii) (4S,5S)-2,2-Dimethyl-4,5-diphenyl-1,3-dioxolane (9a);
(xix) (4S,5R)-2,2-Dimethyl-4,5-diphenyl-1,3-dioxolane (9b);
(xx) 1,3-Dihydro-2H-inden-2-one (4a);
(xxi) 1-Phenyl-1,3-dihydro 2H-inden-2-one (4d);
(xxii) 1-Benzyl-1,3-dihydro-2H-inden-2-one (4e),
(xxiii) 3-propyl-1H-indene (4f);
(xxiv) 1-(3-Chloropropyl)-1,3-dihydro-2H-inden-2-one (4g);
(xxv) 1-(3-Azidopropyl)-1,3-dihydro-2H-inden-2-one (4h);
(xxvi) 1-Phenyl-3,4-dihydronaphthalen-2(1H)-one (4p)
(xxvii) 1-(p-Tolyl)-3,4-dihydronaphthalen-2(1H)-one (4r);
(xxviii) 6-Methoxy-1-phenyl-3,4-dihydronaphthalen-2(1H)-one (4s);
(xxix) 6-Methoxy-1-(p-tolyl)-3,4-dihydronaphthalen-2(1H)-one (4t); and
(xxx) 1-Allyl-1,3-dihydro-2H-inden-2-one (4u).

In another embodiment of the invention the dioxolo compound of benzo-fused cyclic olefins of Formula (I):

Formula (I)

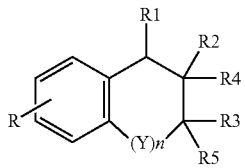

wherein;
R1 and R2, or R2 and R3, or R5 together with —CHR6 represent dioxolo

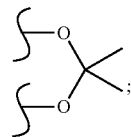

and
R1, or R2, or R3, or R4, or R5 are independently selected from the group consisting of hydrogen, alkoxy, (un)substituted or substituted phenyl, halogen, hydroxy, nitro, amino, carbonyl, —COOH, cyano, azo, (un)substituted or substituted benzyl group,
C1 to C6 cyclo compounds which optionally having one or more heteroatoms selected from N, O or S, heteroaryl, (un)substituted linear or branched alkyl radical having 1 to 10 C atoms, substituted linear or branched alkyl radical having 1 to 10 C atoms, in which one or more CH2 groups optionally independently of one another be replaced by —C═O, —N—, —O—, —S—, —CH═CH—, or —C≡C—, (un)substituted linear or branched alkenyl radical having 1 to 10 C atoms, substituted linear or branched alkenyl radical having 1 to 10 C atoms, (un)substituted linear or branched alkynyl radical having 1 to 10 C atoms, substituted linear or branched alkynyl radical having 1 to 10 C atoms;
'Y' is —CHR6, or heteroatom; wherein R6 is selected from hydrogen, methyl, and phenyl;
R is hydrogen or alkoxy;
'n' is 0 or 1; with the proviso when n=0; Formula I may form five membered ring or three carbon chain; when n=1 Formula I may form six member ring.

In another embodiment of the invention the therapeutic amount of the dioxolo compound as claimed in claim 5 along with pharmaceutically acceptable excipients, for use as an anti-HIV, anti-cancer, or as anti-malarial agent.

DETAILED DESCRIPTION OF THE INVENTION

In view of above, the present invention discloses Oxone-acetone mediated metal free syn-dihydroxylation of benzo-fused cyclic olefins of formula (II)/alkenes of formula (IV).

In an aspect, the present invention provides a process which is stereospecific and does not proceed via the epoxide route.

The present inventors after exhaustive experimentation identified the optimized conditions that can drive the Oxone-acetone mediated reaction of benzo fused cycloalkenes/stilbene and its derivatives exclusively towards the syn-dihydroxylation without proceeding the epoxide route. Unlike the use of acetone as a reagent for epoxidation in prior art process the optimized conditions employed in syn dihydroxylation uses acetone as the solvent. Further, both the base and Oxone are employed in the same molar proportions, like in the case of epoxidation, the controlled experiments revealed that the presence of ethyl acetate is also essential.

The present invention disclose the optimized reaction conditions involving the addition of 2 equivalents of powdered Oxone (H3K5S4O18) to stirred slurry of 3 equivalents of sodium bicarbonate (NaHCO3) and 1 equivalent of benzo fused cycloalkenes of formula II/or alkenes of formula III in a mixture of solvents 5:1:1 (acetone+ethyl acetate+water) at ambient temperature and pressure to obtain library of dioxolo compounds/acetonides of formula (I) or formula (IV) respectively.

The present invention relates to simple, one step, oxone-acetone mediated metal free syn-dihydroxylation process at ambient temperature and pressure for synthesis of dioxolo compounds of benzo-fused cyclic olefins of formula (I);

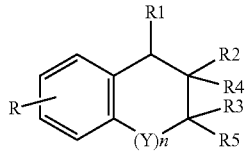

Formula (I)

wherein;
R1 and R2 or R2 and R3 or R5 together with —CHR6 represent dioxolo

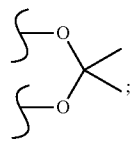

R is selected from hydrogen or alkoxy;
R1 or R2 or R3 or R4 or R5 which do not form the dioxolo group is selected independently of each other from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl, a linear or branched alkyl radical having 1 to 10 C atoms which is (un)substituted or substituted; in which one or more CH2 groups may each, independently of one another, be replaced by —C=O, —N—, —O— or —S—, —CH=CH—, —C≡C—; a linear or branched alkenyl radical having 1 to 10C atoms which is (un)substituted or substituted; a linear or branched alkynyl radical having 1 to 10C atoms which is (un)substituted or substituted;
'Y' is —CHR6 or heteroatom; wherein R6 is hydrogen or methyl or phenyl;
'n' is 0 or 1;
with the proviso when
'n' is 0
R2 and R3 together represent dioxolo

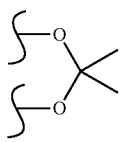

R is selected from hydrogen or alkoxy;
R1, R4 and R5 are selected independently of each other from hydrogen, alkoxy, phenyl which is (un)substituted or substituted, halogen, hydroxy, carbonyl, -azo, benzyl group which is (un)substituted or substituted; C1 to C6 cyclo compounds a linear or branched alkyl radical having 1 to 8C atoms which is (un)substituted or substituted; in which one or more CH2 groups may each, independently of one another, —CH=CH—, —C≡C—; a linear or branched alkenyl radical having 1 to 8C atoms which is (un)substituted or substituted; a linear or branched alkynyl radical having 1 to 10C atoms which is (un)substituted or substituted;
with the proviso when,
'n' is 0
R3 represent dioxolo

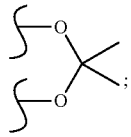

R is selected from hydrogen or alkoxy;
R1, R2, R4 and R5 are selected independently of each other from hydrogen, alkoxy, phenyl which is (un)substituted or substituted, halogen, azo, benzyl group which is (un)substituted or substituted; C1 to C6 cyclo compounds a linear or branched alkyl radical having 1 to 8C atoms which is (un)substituted or substituted; in which one or more CH2 groups may each, independently of one another, —CH=CH—, —C≡C—; a linear or branched alkenyl radical having 1 to 10C atoms which is (un)substituted or substituted; a linear or branched alkynyl radical having 1 to 8C atoms which is (un)substituted or substituted;
with the proviso when,
'n' is 1
'Y' is carbon
R1 and R2 together represent dioxolo

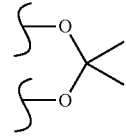

R is selected from hydrogen or alkoxy;
R3, R4 and R5 are selected independently of each other from hydrogen, alkoxy, phenyl which is (un)substituted or substituted, halogen, carbonyl, -, azo, benzyl group which is (un)substituted or substituted; C1 to C6 cyclo compounds a linear or branched alkyl radical having 1 to 10C atoms which is (un)substituted or substituted; in which one or more CH2 groups may each, independently of one another, be replaced by —CH=CH—, —C≡C—; a linear or branched alkenyl radical having 1 to 10C atoms which is (un)substituted or substituted; a linear or branched alkynyl radical having 1 to 10C atoms which is (un)substituted or substituted; with the proviso when
'n' is 1
'Y' is —CHR6, wherein R6 is hydrogen or methyl or phenyl;
R5 together with —CHR6 represent a dioxolo

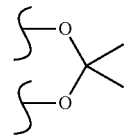

R is selected from hydrogen or alkoxy;
R1, R2, R3 and R4 are selected independently of each other from hydrogen, alkoxy, phenyl which is (un)substituted or substituted, halogen, carbonyl, azo, benzyl group which is (un)substituted or substituted; C1 to C6 cyclo compounds which may have one or more heteroatoms selected from N, O or S; a heteroaryl; a linear or branched alkyl radical having 1 to 8C atoms which is (un)substituted or substituted; in which one or more CH2 groups may each, independently of one another, —CH=CH—, —C≡C—; a linear or branched alkenyl radical having 1 to 10C atoms which is (un)substituted or substituted; a linear or branched alkynyl radical having 1 to 8C atoms which is (un)substituted or substituted;
which comprises;
reacting compound of formula (II)

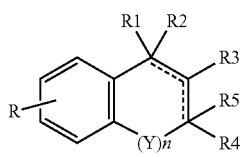

(II)

wherein,
R is selected from hydrogen or alkoxy,
R1, R2, R3, R4 and R5 are selected independently of each other from hydrogen, alkoxy, phenyl which is (un)substituted or substituted, halogen, carbonyl, -, azo, benzyl group which is (un)substituted or substituted; C1 to C6 cyclo compounds a linear or branched alkyl radical having 1 to 10C atoms which is (un)substituted or substituted; in which one or more CH2 groups may each, independently of one another, be replaced by —CH=CH—, —C≡C—; a linear or branched alkenyl radical having 1 to 8C atoms which is (un)substituted or substituted; a linear or branched alkynyl radical having 1 to 8C atoms which is (un)substituted or substituted;
'Y' is —CHR6 or heteroatom; wherein R6 is hydrogen or methyl or phenyl;
'n' is 0 or 1; 'the dotted lines' represents a double or single bond;
with 2 equivalents of powdered Oxone (H3K5S4O18) and 3 equivalents of sodium bicarbonate (NaHCO3) in a mixture of solvents 5:1:1 (acetone+ethyl acetate+water); stirring the contents at room temperature for 2-5 h; evaporating the excess acetone under reduced pressure on completion of reaction; portioning the remaining reaction mixture between water and ethyl acetate followed by purification.

The present invention provide dioxolo compounds of benzo-fused cyclic olefins of formula (I);

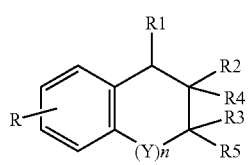

(I)

wherein;
R1 and R2 or R2 and R3 or R5 together with —CHR6 represent dioxolo

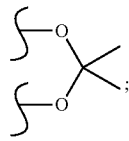

R is selected from hydrogen or alkoxy;
R1 or R2 or R3 or R4 or R5 which do not form the dioxolo group is selected independently of each other from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl; a linear or branched alkyl radical having 1 to 10 C atoms which is (un)substituted or substituted; in which one or more CH2 groups may each, independently of one another, be replaced by —C=O, —N—, —O— or —S—, —CH=CH—, —C≡C—; an alkenyl radical having 1 to 10 C atoms which is (un)substituted or substituted; an alkynyl radical having 1 to 10 C atoms which is (un)substituted or substituted;
'Y' is —CHR6 or heteroatom; wherein R6 is hydrogen or methyl or phenyl;
'n' is 0 or 1;
with the proviso when
'n' is 0
R2 and R3 together represent dioxolo

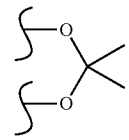

R is selected from hydrogen or alkoxy;
R1, R4 and R5 are selected independently of each other from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl; a linear or branched alkyl radical having 1 to 10C atoms which is (un)substituted or substituted; in which one or more CH2 groups may each, independently of one another, be replaced by —C=O, —N—, —O— or —S—, —CH=CH—, —C≡C—; a linear or branched alkenyl radical having 1 to 10C atoms which is (un)substituted or substituted; a linear or branched alkynyl radical having 1 to 10C atoms which is (un)substituted or substituted;
with the proviso when,
'n' is 0
R3 represent dioxolo

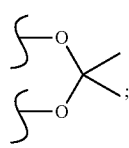

R is selected from hydrogen or alkoxy;
R1, R2, R4 and R5 are selected independently of each other from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl; a linear or branched alkyl radical having 1 to 10C atoms which is (un)substituted or substituted; in which one or more CH2 groups may each, independently of one another, be replaced by —C=6, —N—, —O— or —S—, —CH=CH—, —C≡C—; a linear or branched alkenyl radical having 1 to 10C atoms which is (un)substituted or substituted; a linear or branched alkynyl radical having 1 to 10C atoms which is (un)substituted or substituted;
with the proviso when,
'n' is 1
'Y' is heteroatom
R1 and R2 together represent dioxolo

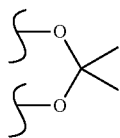

R is selected from hydrogen or alkoxy;
R3, R4 and R5 are selected independently of each other from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl; a linear or branched alkyl radical having 1 to 10C atoms which is (un)substituted or substituted; in which one or more CH2 groups may each, independently of one another, be replaced by —C=O, —N—, —O— or —S—, —CH=CH—, —C≡C—; a linear or branched alkenyl radical having 1 to 10C atoms which is (un)substituted or substituted; a linear or branched alkynyl radical having 1 to 10C atoms which is (un)substituted or substituted;
with the proviso when
'n' is 1
'Y' is —CHR6, wherein R6 is hydrogen or methyl or phenyl;
R5 together with —CHR6 represent a dioxolo

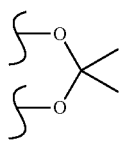

R is selected from hydrogen or alkoxy;
R1, R2, R3 and R4 are selected independently of each other from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl; a linear or branched alkyl radical having 1 to 10C atoms which is (un)substituted or substituted; in which one or more CH2 groups may each, independently of one another, be replaced by —C=O, —N—, —O— or —S—, —CH=CH—, —C≡C—; a linear or branched alkenyl radical having 1 to 10C atoms which is (un)substituted or substituted; a linear or branched alkynyl radical having 1 to 10C atoms which is (un)substituted or substituted;

The dioxolo compounds of formula (I) of the present invention comprises:
2,2-dimethyl-8,8a-dihydro-3aH-indeno[1,2-d][1,3]dioxole (2a);
2,2-dimethyl-3a-propyl-8,8a-dihydro-3aH-indeno[1,2-d][1,3]dioxole (2b):
3a-(3-chloropropyl)-2,2-dimethyl-8,8a-dihydro-3aH-indeno[1,2-d][1,3]dioxole (2c):—
8-(4-bromobutyl)-2,2-dimethyl-8,8a-dihydro-3aH-indeno[1,2-d][1,3]dioxole (2d):—
8-benzyl-2,2-dimethyl-8,8a-dihydro-3aH-indeno[1,2-d][1,3]dioxole (2e):—
3a-benzyl-2,2-dimethyl-8,8a-dihydro-3aH-indeno[1,2-d][1,3]dioxole (2f):—
3a-isopropyl-2,2-dimethyl 8,8a dihydro 3aH-indeno[1,2-d][1,3]dioxole (2g):
3a-cyclohexyl-2,2-dimethyl-8,8a-dihydro-3aH-indeno[2,1-d][1,3]dioxole (2h):
2,2-dimethyl-3a-phenyl-8,8a-dihydro-3aH-indeno[1,2-d][1,3]dioxole (2i):—
7-(2,2-dimethyl-8,8a-dihydro-3aH-indeno[2,1-d][1,3]dioxol-3a-yl)heptan-2-one (2j):—
2',2'-dimethyl-3a',8a'-dihydrospiro[cyclopentane-1,8'-indeno[2,1-d][1,3]dioxole](2k):—
3a-(but-3-enyl)-2,2-dimethyl-8,8a-dihydro-3aH-indeno[2,1-d][1,3]dioxole (2m):—
2,2,9b-Trimethyl-3a,4,5,9b-tetrahydronaphtho[2,1-d][1,3]dioxole (2o):—
7-Methoxy-2,2,9b-trimethyl-3a,4,5,9b-tetrahydronaphtho[1,2-d][1,3]dioxole (2p):
2,2-Dimethyl-9b-phenyl-3a,4,5,9btetrahydronaphtho[2,1-d][1,3]dioxole (2q):—
7-Methoxy-2,2-dimethyl-9b-phenyl-3a,4,5,9b-tetrahydronaphtho[1,2-d][1,3]dioxole (2r):—
2,2-dimethyl-3a-(2-(oxiran-2-yl)ethyl)-3a,8a-dihydro-8H-indeno[1,2-d][1,3]dioxole (6):—
4S,5 S)-2,2-Dimethyl-4,5-diphenyl-1,3-dioxolane (9a);
(4S,5R)-2,2-Dimethyl-4,5-diphenyl-1,3-dioxolane (9b);
In one embodiment, the benzo-fused cyclic olefin is selected from indene or substituted indenes.

The general scheme for synthesis of compounds of Formula (I) from compounds of Formula II is set forth in Scheme 1 below:

Scheme 1

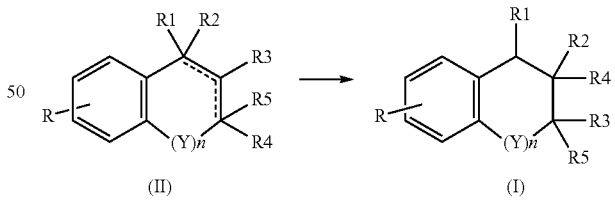

wherein;
R1 and R2, or R2 and R3, or R5 together with —CHR6 represent dioxolo

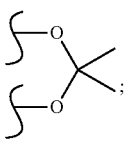

R is hydrogen or alkoxy;

R1, or R2, or R3, or R4, or R5 which do not form the dioxolo group is independently selected from the group consisting of hydrogen, alkoxy (un)substituted or substituted phenyl, halogen, hydroxy, nitro, amino, carbonyl, —COOH, cyano, azo, (un)substituted or substituted benzyl group, C1 to C6 cyclo compounds which may have one or more heteroatoms selected from N, O or S, heteroaryl, (un)substituted linear or branched alkyl radical having 1 to 10 C atoms, substituted linear or branched alkyl radical having 1 to 10 C atoms, in which one or more CH2 groups may each independently of one another be replaced by —C=O, —N—, —O—, —S—, —CH=CH—, or —C≡C—, linear or branched alkenyl radical having 1 to 10 C atoms which is (un)substituted or substituted, linear or branched alkynyl radical having 1 to 10 C atoms which is (un)substituted or substituted;

'Y' is —CHR6, or heteroatom; wherein R6 is selected from hydrogen, methyl, and phenyl;

'n' is 0 or 1; with the proviso when n=0; Formula I may form five membered ring or three carbon chain; when n=1 Formula I may form six member ring.

Accordingly, the process for synthesis of dioxolo compounds/acetonide from simple indene or its derivatives comprising adding 2 equivalents of powdered Oxone (H3K5S4O18) to a stirred slurry of 3 equivalents of sodium bicarbonate (NaHCO3) and indene or its derivative of formula (V) to a mixture of solvents 5:1:1 (acetone+ethyl acetate+water); stirring the mixture at room temperature for 2-5 h; evaporating the excess acetone under reduced pressure on completion of reaction; portioning the remaining reaction mixture between water and ethyl acetate followed by purification to obtain acetonide/dioxolo compounds of formula (VI).

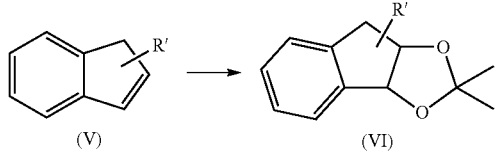

wherein R' represent independently of each other groups selected from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl; a linear or branched alkyl radical having 1 to 10 C atoms which is (un)substituted or substituted; in which one or more CH2 groups may each, independently of one another, be replaced by —C=O, —N—, —O— or —S—, —CH=CH—, —C≡C—; a linear or branched alkenyl radical having 1 to 10 C atoms which is (un)substituted or substituted; a linear or branched alkynyl radical having 1 to 10C atoms which is (un)substituted or substituted.

With simple indene, the reaction was completed within 4 h and the required 2a has been formed as the sole product in 82% yield.

The process is depicted below in Scheme 2:

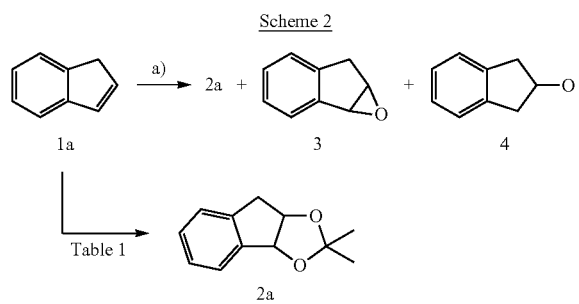

a) Indene (1 eqv.), Oxone (2 eqv.), Sodium bicarbonate (5 eqv.), Acetone (10 eqv.), Water + Ethyl acetate (1:1)

TABLE 1

Reaction Optimization

| Sr. No. | Oxone (equiv) | NaHCO$_3$ (equiv) | % of Conversion | % Yield[b] (2a) |
|---|---|---|---|---|
| 1 | 0.5 | 1 | 10 | — |
| 2 | 0.5 | 2 | 25 | 20[c] |
| 3 | 0.5 | 3 | 40 | —[d] |
| 4 | 1 | 3 | 40 | 12[c] |
| 5 | 2 | 3 | 100 | 82 |
| 6 | 2 | 2 | 90 | 71 |
| 7 | 3 | 3 | 100 | 82 |
| 8 | 4 | 3 | 100 | 70[c] |
| 9 | 4 | 5 | 100 | 55[c] |

[a]Reactions are carried out at room temperature with 0.1 mmol of indene in 2.5 ml acetone 1 ml water + ethyl acetate (1:1).
[b]Isolated yield.
[c]Mixture of products (2a + 3 + 4).
[d]4 was obtained in 35% isolated yield.

TABLE 2

Generality of Oxone-mediated syn-dihydroxylation of various Indene derivatives

| S. No. | Substrate | Product (Yield) |
|---|---|---|
| 1 | 1b | 2b (78%) |

TABLE 2-continued

Generality of Oxone-mediated syn-dihydroxylation of various Indene derivatives

| S. No. | Substrate | Product (Yield) |
|---|---|---|
| 2 | 1c | 2c (69%) |
| 3 | 1d | 2d (77%) |
| 4 | 1e | 2e (77%) |
| 5 | 1f | 2f (75%) |
| 6 | 1g | 2g (63%) |
| 7 | 1h | 2h (65%) |

TABLE 2-continued

Generality of Oxone-mediated syn-dihydroxylation of various Indene derivatives

| S. No. | Substrate | Product (Yield) |
|---|---|---|
| 8 | 1i | 2i (61%) |
| 9 | 1j | 2j (70%) |
| 10 | 1k | 2k (73%) |
| 11 | 1l | 5 (15%) |
| 12 | 1m | 2m (73%) |
| 13 | 2m | 6 (85%) |

TABLE 2-continued

Generality of Oxone-mediated syn-dihydroxylation of various Indene derivatives

| S. No. | Substrate | Product (Yield) |
|---|---|---|
| 14 | 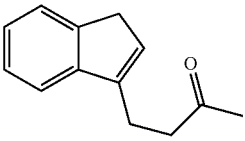<br>1n | 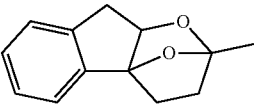<br>7 (64%) |

The present invention provides a process for the synthesis of substituted indenes, preferably alkyl indene comprising the steps of:
a. Adding NaH to a suspension of indene and alkyl bromide in DMF at 0° C. followed by stirring the reaction mixture for 3 h at room temperature;
b. Quenching the reaction mixture of step (a) with cold water at 0° C. followed by portioned between water and ethyl acetate and purifying to obtain compounds of formula (VI).

The process for the synthesis of substituted indenes is shown below in Scheme 3:

Scheme 3

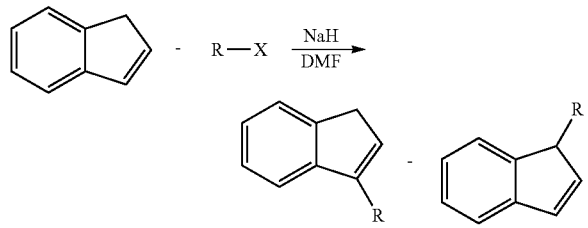

wherein, R is an alkyl and X is halogen:

The present invention discloses syn-dihydroxylation of dihydronaphthalene derivatives of formula (VII).

Accordingly, the process comprises adding 2 equivalents of powdered Oxone (H3K5S4O18) to a stirred slurry of 3 equivalents of sodium bicarbonate (NaHCO3) and dihydronaphthalene derivatives of formula (VII) to a mixture of solvents 5:1:1 (acetone+ethyl acetate+water); stirring the mixture at room temperature for 2-5 h; evaporating the excess acetone under reduced pressure on completion of reaction, portioning the remaining reaction mixture between water and ethyl acetate followed by purification to obtain acetonide/dioxolo compounds of formula (VIII).

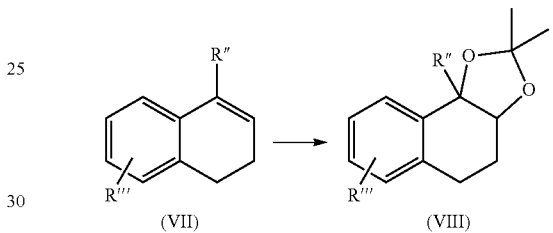

wherein
R''' is selected from hydrogen or alkoxy;
R'' represent independently of each other groups selected from hydrogen, alkoxy, phenyl which is (un)substituted or substituted, halogen, hydroxy, nitro, amino, carbonyl, —COOH, cyano, azo, benzyl group which is (un)substituted or substituted; C1 to C6 cyclo compounds which may have one or more heteroatoms selected from N, O or S; a heteroaryl; a linear or branched alkyl radical having 1 to 10C atoms which is (un)substituted or substituted; in which one or more CH2 groups may each, independently of one another, be replaced by —C=O, —N—, —O— or —S—, —CH=CH—, —C≡C—; a linear or branched alkenyl radical having 1 to 10C atoms which is (un)substituted or substituted; a linear or branched alkynyl radical having 1 to 10 C atoms which is (un)substituted or substituted.

TABLE 3

The Scope of Oxone-acetone mediated syn-dihydroxylation reaction with various dihyronaphthalene derivatives

| Entry | Substrate | | Product | | Yield[b] (%) |
|---|---|---|---|---|---|
| | 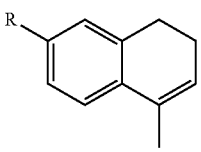 | | 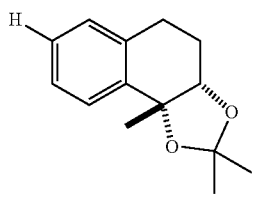 | | |
| 1 | R=H | 1o | | 2o | 65 |
| 2 | R=OMe | 1p | | 2p | 71 |

TABLE 3-continued

The Scope of Oxone-acetone mediated syn-dihydroxylation reaction with various dihyronaphthalene derivatives

| Entry | Substrate | | Product | | Yield[b] (%) |
|---|---|---|---|---|---|
| 3 | R=H | 1q | | 2q | 60 |
| 4 | R=OMe | 1r | | 2r | 64 |

The present invention provides a simple, one step oxone-acetone mediated, metal free syn-dihydroxylation process for synthesis of dioxolo compounds of formula (IV) at ambient temperature and pressure, (IV)

wherein
R is selected from aryl or benzyl;
comprising;
Reacting compound of formula (III)

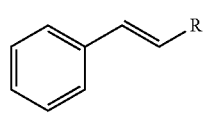

(III)

wherein,
R is selected from aryl or benzyl;
with 2 equivalents of powdered Oxone (H3K5S4O18) and 3 equivalents of sodium bicarbonate (NaHCO3) in a mixture of solvents 5:1:1 (acetone+ethyl acetate+water) and stirring the contents at room temperature for 2-5 h; evaporating the excess acetone under reduced pressure on completion of reaction, portioning the remaining reaction mixture between water and ethyl acetate followed by purification.

The present invention relate to Oxone-acetone mediated syn-dihydroxylation reaction of cis and trans stilbene comprising reacting cis or trans stibene with 2 equivalents of powdered Oxone (H3K5S4O18)+ and 3 equivalents of sodium bicarbonate (NaHCO3) in a mixture of solvents 5:1:1 (acetone+ethyl acetate+water) and stirring the contents at room temperature for 2-5 h; evaporating the excess acetone under reduced pressure on completion of reaction, portioning the remaining reaction mixture between water and ethyl acetate followed by purification.

The reactions are observed to be completely stereospecific. The trans-stilbene gave exclusively the corresponding trans-acetonide and trans-epoxide in moderate yields. Similarly, cis-stilbene gave the corresponding cis-acetonide and cis-epoxide.

TABLE 4

The Scope of Oxone-acetone mediated syn-dihydroxylation reaction of cis and trans stilbene.

| Entry | Reactant | Product (with yield) |
|---|---|---|
| 1. | | 44%   36% |
| 2. | | 36%   30% |

The present invention demonstrates a simple method for the metal-free syn-dihydroxylation of the benzo-fused cyclic olefins/stilbenes employing Oxone. The reactions are highly selective towards the syn-dihydroxylation and the corresponding acetonides are isolated in excellent yields. The conditions are tolerable for the other functional groups on the side chains such as chloro, bromo, carbonyl and even olefin.

For instance, in case of the indene (1m) having an alkenyl group at C2, the acetonide (2m) was isolated as the sole product, leaving the pendant alkenyl group intact. When (2m) was treated again with Oxone under the same conditions, the corresponding diastereomeric epoxides (6) were isolated. The reaction with tetra substituted indene (11) was sluggish and gave exclusively the diketo derivative (5) as the main product. The 4-H (1H-inden-3-yl) butan-2-one (1n) when treated with oxone in acetone gave the inseparable mixture of compounds. Whereas, when acetone was replaced with acetonitrile, the 2,7-dioxabicyclo[2.2.1]heptane derivative (7) was obtained in good yield.

Further, the dihydronaphthalene derivatives also underwent the syn-dihydroxylation smoothly and provided the corresponding acetonides in good yields. Similarly, the reaction with stilbenes 14a and 14b are sluggish and gave a mixture of epoxide and acetonide. However, these reactions are completely stereospecific. The trans-stilbene derivative 14a gave exclusively the corresponding trans-acetonide and trans-epoxide derivatives 15a and 15a' in moderate yields, similarly cis-stilbene 14b gave cis-acetonide and cis-epoxide derivatives 15b and 15b' in moderate yields. The 1-methylene-2,3-dihydro-1H-indene (compound 1m, table 2) gave the corresponding acetonide (2m, table 3) in very good yields. Amongst the two chromenes employed (table 5), the reaction with 2,2-dimethyl-2H-chromene 16a resulted in an inseparable mixture of corresponding epoxide and acetonides 17a' and 17a in a 3:1 ratio. Whereas, there was no reaction with the 2,2-diphenyl-2H-chromene 16b.

TABLE 5

Generality of Oxone-mediated syn-dihydroxyation of various benzo-fused cyclic olefins of formula (II) and alkenes of formula (IV)

| S. No. | Substrate | Product (Yield) |
|---|---|---|
| 1 | 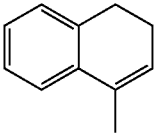 8a | 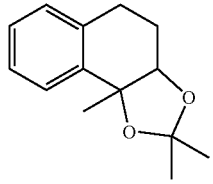 [SMILES: CC1(C)OC2CCc3ccccc3C2(C)O1] 9a (65%) |
| 2 | 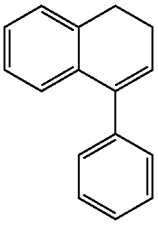 [SMILES: C1=C(c2ccccc2)c2ccccc2CC1] 8b | 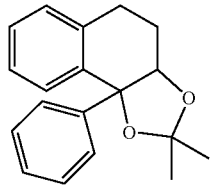 [SMILES: CC1(C)OC2CCc3ccccc3C2(c2ccccc2)O1] 9b (60%) |
| 3 | 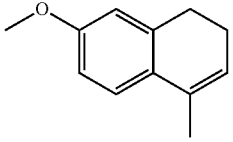 8c | 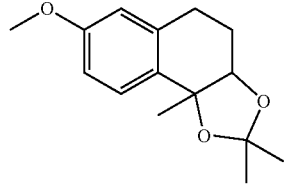 9c (72%) |
| 4 | 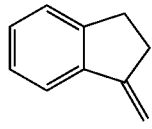 10 | 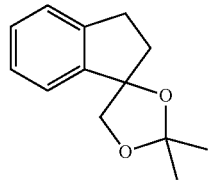 11 (58%) |
| 5 | 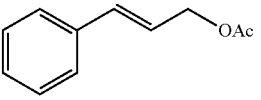 [SMILES: CC(=O)OC/C=C/c1ccccc1] 12 | 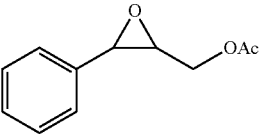 [SMILES: CC(=O)OCC1OC1c1ccccc1] 13 (86%) |

TABLE 5-continued

Generality of Oxone-mediated syn-dihydroxyation of various benzo-fused cyclic olefins of formula (II) and alkenes of formula (IV)

| S. No. | Substrate | Product (Yield) |
|---|---|---|
| 6 | 14a | 15a (48%)   15a' (35%) |
| 7 | 14b | 15b (35%)   15b' (35%) |
| 8 | (R=—Me) 16a | 17a (10%)   17a' (30%) |
| 9 | (R=—Ph) 16b | (No Reaction) |

Furthermore, the inventors observed that by varying the proportion of the base employed i.e NaHCO3 complete conversion to ketone (Wacker type oxidation) in good to excellent yields can be achieved. The use of 12 eq. of base along with 2 eq. of Oxone was found to be the key for the complete conversion.

The present invention discloses a simple process for preparation of compound of formula (X);

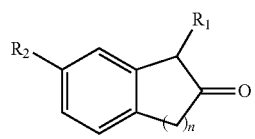

Formula (X)

wherein,
R1 is selected independently of each other from the group consisting of hydrogen, alkyl or aryl; R2 is hydrogen or alkoxy; and
'n' is 1 or 2;

Comprising reacting compound of formula (IX)

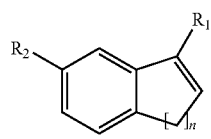

(IX)

wherein R1, R2 and 'n' are as defined above with 2 equivalents of powdered Oxone (H3K5S4O18) and 12 equivalents of sodium bicarbonate (NaHCO3) in a mixture of solvents 5:1:1 (acetone+ethyl acetate+water) and stirring the contents at room temperature for 2-5 h; evaporating the excess acetone under reduced pressure on completion of reaction, portioning the remaining reaction mixture between water and ethyl acetate followed by purification.

TABLE 6

Scope of Wacker-type oxidation reaction

| Entry | Substrate | | Product | | Yield[b] (%) |
|---|---|---|---|---|---|
| 1 | R=H | 1a | 4a | | 78 |
| 2 | R=Ph | 1d | 4d | | 61 |
| 3 | R=CH$_2$Ph | 1e | 4e | | 75 |
| 4 | R=(CH$_2$)$_3$Cl | 1g | 4g | | 74 |
| 5 | R=(CH$_2$)$_3$N$_3$ | 1h | 4h | | 72 |
| 6 | R=(CH$_2$)$_2$CH$_3$ | 1f | 4f | | 74 |
| 7 | | 1i | | 4f | 78 |
| 8 | R=H | 1p | 4p | | 65 |
| 9 | R=OMe | 1r | 4r | | 72 |
| 10 | R=H | 1s | 4s | | 61 |
| 11 | R=OMe | 1t | 4t | | 69 |

The compounds of formula (X) comprises:
(i) 1,3-Dihydro-2H-inden-2-one (4a);
(ii) 1-Phenyl-1,3-dihydro-2H-inden-2-one (4d);
(iii) 1-Benzyl-1,3-dihydro-2H-inden-2-one (4e);
(iv) 3-propyl-1H-indene (4f);
(v) 1-(3-Chloropropyl)-1,3-dihydro-2H-inden-2-one (4g);
(vi) 1-(3-Azidopropyl)-1,3-dihydro-2H-inden-2-one (4h);
(vii) 1-Phenyl-3,4-dihydronaphthalen-2(1H)-one (4p)
(viii) 1-(p-Tolyl)-3,4-dihydronaphthalen-2(1H)-one (4r);
(ix) 6-Methoxy-1-phenyl-3,4-dihydronaphthalen-2(1H)-one (4s);
(x) 6-Methoxy-1-(p-tolyl)-3,4-dihydronaphthalen-2(1H)-one (4t);
(xi) 1-Allyl-1,3-dihydro-2H-inden-2-one (4u)

The library of dioxolo compounds/acetonides of formula (I) prepared by the simple, stereospecific process of the present invention finds use as anti-HIV, anti-cancer and as anti-malarials and may be further converted to its pharmaceutically active salts and may be thereafter incorporated in a pharmaceutical composition along with suitable pharmaceutical excipients for therapeutic use.

Further, the library of dioxolo compounds/acetonides of formula (I) prepared by the simple, stereospecifc process of the present invention can be used as ligand for many other industrial applications.

Further, the instant invention reveal that by simple variation in reaction conditions both dihydroxylations and the Wacker type of oxidation of benzo-fused olefins can be conducted selectively, apart from their well-established epoxidation.

EXAMPLES

The following examples are given by way of illustration of the working of the invention in actual practice and therefore should not be construed to limit the scope of the present invention.

Example 1

General Methods

All commercial solvents and reagents were used without purification. Column chromatography was carried out by using spectrochem silica gel (60-120, 100-200, 230-400 mesh). $^1$H and $^{13}$C NMR chemical shifts are reported in ppm downfield from Chloroform-d (δ=7.25) or TMS and coupling constants (J) are reported in Hertz (Hz). The following abbreviations are used to designate signal multiplicity: s=singlet, d=doublet, t=triplet, q=quartet, m=multiplet, b=broad. The Multiplicity of $^{13}$C NMR signals was assigned with the help of DEPT spectra and the carbons represent C (quaternary), CH, CH$_2$ and CH$_3$ respectively.

Example 2

General Procedure for Substituted Indenes (A)

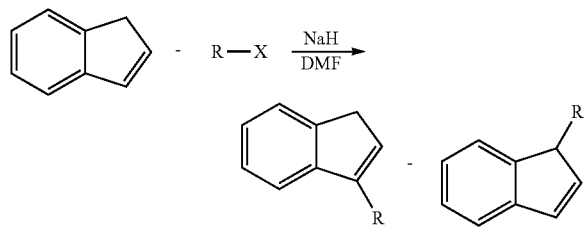

NaH (1.2 eq) was added to suspension of indene (1.0 eq) and alkyl bromide (1.1 eq) in DMF at 0° C. and the reaction mixture was stirred for 3 h at room temperature. The reaction mixture was quenched with cold water at 0° C. and portioned between water and ethyl acetate. The organic phase was separated and the aqueous phase was extracted with ethyl acetate (2×50 mL). The combined organic phase was washed with brine, dried (Na$_2$SO$_4$) and concentrated under reduced pressure. The crude product was purified by silica gel column (ethyl acetate and pet ether as eluent) to afford substituted indene.

Example 3

General Procedure for Syn-Dihydroxylation (B)

To a solution of indene or substituted indene (1 eq.) in acetone (10 mL, for 1 mmol indene) were added ethyl acetate (2 mL), water (2 mL) and solid NaHCO$_3$ (3 eq.) and the reaction mixture was stirred for 10 min. To this was added solid Oxone (2 eq.) and contents were stirred at room temperature for 2-5 h. After completion of the reaction, the excess acetone evaporated under reduced pressure and remaining reaction mixture portioned between water and ethyl acetate (20 mL each). The organic layer was separated and the aqueous layer extracted with ethyl acetate (2×20 mL). Combined organic layer was dried (Na$_2$SO$_4$) and concentrated under reduced pressure. The crude product was purified by silica gel column (ethyl acetate and pet ether as eluent) to afford the corresponding acetonide.

Example 4

General Procedure for Ketone (C)

To a solution of indene (1 eq.) in acetone (10 mL, for 1 mmol indene) were added ethyl acetate (2 mL), water (2 mL) and solid NaHCO$_3$ (12 eq.) and the reaction mixture was stirred for 10 min. To this was added solid Oxone (2 eq.) and contents were stirred at room temperature for 15-18 h. After completion of the reaction, the excess acetone evaporated under reduced pressure and remaining reaction mixture portioned between water and ethyl acetate (20 mL each). The organic layer was separated and the aqueous layer extracted with ethyl acetate (2×20 mL). Combined organic layer was dried (Na$_2$SO$_4$) and concentrated under reduced pressure. The crude product was purified by silica gel column (ethyl acetate and pet ether as eluent) to afford the corresponding ketone.

2,2-dimethyl-8,8a-dihydro-3aH-indeno[1,2-d][1,3] dioxole (2a)

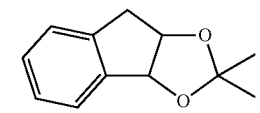

The general procedure B was followed using (indene) 1a (100 mg, 0.86 mmol) as a substrate procured 2a (134 mg, 82%) as a white solid; R$_f$ 0.3 (5% ethyl acetate/pet. ether); mp: 65-68° C.; IR (CHCl$_3$)ν: 3018, 2934, 1608, 1460, 1372, 1216, 1056, 1018, 863, 758, 668 cm$^{-1}$; $^1$H NMR (200 MHz, CDCl$_3$): δ=1.21 (s, 3H), 1.40 (s, 3H), 3.14 (dd, J=2.2, 4.2 Hz, 2H), 4.99 (ddd, J=2.2, 4.2, 5.6 Hz, 1H), 5.54 (d, J=5.6 Hz 1H), 7.20-7.28 (m, 3H), 7.39-7.42 (m, 1H); $^{13}$C-NMR (50 MHz, CDCl$_3$): δ=25.9 (CH$_3$), 27.5 (CH$_3$), 37.8 (CH$_2$), 79.4 (CH), 84.0 (CH), 110.7 (C), 125.4 (CH), 125.7 (3CH), 127.2 (CH), 128.9 (CH), 140.9 (C), 141.4 (C). (C$_{12}$H$_{14}$O$_2$)

2,2-dimethyl-3a-propyl-8,8a-dihydro-3aH-indeno[1, 2-d][1,3]dioxole (2b)

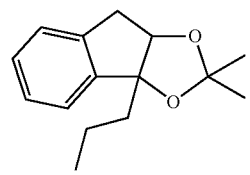 [SMILES: CCCC12OC(C)(C)OC1Cc1ccccc12]

The general procedure B was followed using (3-propyl-1H-indene) 1b (100 mg, 0.52 mmol) as a substrate procured 2b (108 mg, 78%) as a colourless liquid; R$_f$ 0.3 (5% ethyl acetate/pet. ether); IR (CHCl$_3$)ν: 3026, 2984, 2933, 1607, 1459, 1368, 1247, 1126, 1057, 910, 848, 723 cm$^{-1}$; $^1$H NMR (400 MHz, CDCl$_3$): δ=0.91 (t, J=7.3 Hz, 3H), 1.05 (s, 3H), 1.19 (ddq, J=5.3, 7.3, 12.5 Hz, 1H),1.36-1.39 (m, 1H), 1.42 (s, 3H), 1.86 (ddd, J=2.2, 4.7, 12.6 Hz, 1H), 1.94 (ddd, J=2.2, 4.7, 12.6 Hz, 1H), 3.07 (d, J=2.4 Hz, 2H), 4.61 (t, J=2.4 Hz, 1H), 7.16-7.20 (m, 1H), 7.24-7.27 (m, 2H), 7.33-7.35 (m, 1H); $^{13}$C-NMR (100 MHz, CDCl$_3$): δ=14.4 (CH$_3$), 17.5 (CH$_2$), 27.5 (CH$_3$), 27.8 (CH$_3$), 37.1 (CH$_2$), 39.9 (CH$_2$), 83.5 (CH), 93.8 (C), 110.0 (C), 124.1 (CH), 125.3 (CH), 127.1 (CH), 128.4 (CH), 140.0 (C), 145.4 (C). (C$_{15}$H$_{20}$O$_2$)

3a-(3-chloropropyl)-2,2-dimethyl-8,8a-dihydro-3aH-indeno[1,2-d][1,3]dioxole (2c)

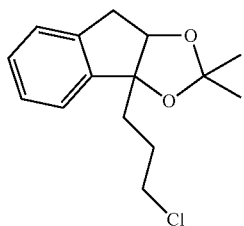 [SMILES: CC1(C)OC2Cc3ccccc3C2(CCCCl)O1]

The general procedure B was followed using (3-(3-chloropropyl)-1H-indene) 1c (100 mg, 0.52 mmol) as a substrate procured 2c (96 mg, 69%) as a yellow liquid; R$_f$ 0.3 (10% ethyl acetate/pet. ether); IR (CHCl$_3$)v: 3355, 3065, 2956, 1711, 1604, 1457, 1396, 1295, 1018, 770, 720 cm$^{-1}$; $^1$H NMR (400 MHz, CDCl$_3$): δ=1.03 (s, 3H), 1.40 (s, 3H), 1.70-1.82 (m, 1H), 1.90-2.06 (m, 3H), 3.07 (d, J=2.5 Hz, 2H), 3.36-3.41 (m, 1H), 3.50-3.55 (m, 1H), 4.59 (dd, J=2.5, 3.9 Hz, 1H), 7.22 (dd, J=2.7, 7.6 Hz, 1H), 7.26 (dd, J=2.7, 5.6 Hz, 2H), 7.34 (dd, J=2.5, 7.6 Hz, 1H); $^{13}$C-NMR (100 MHz, CDCl$_3$): δ=27.5 (CH$_3$), 27.8 (CH$_3$), 33.7 (CH$_2$), 34.8 (CH$_2$), 37.0 (CH$_2$), 45.1 (CH2), 83.5 (CH), 93.1 (C), 110.4 (C), 124.1 (CH), 125.5 (CH), 127.3 (CH), 128.7 (CH), 139.9 (C), 144.8 (C). (C$_{15}$H$_{19}$ClO$_2$)

8-(4-bromobutyl)-2,2-dimethyl-8,8a-dihydro-3aH-indeno[1,2-d][1,3]dioxole (2d)

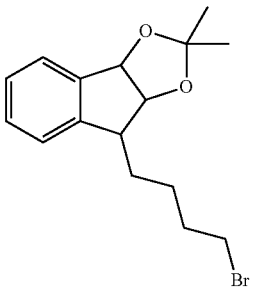 [SMILES: CC1(C)OC2c3ccccc3C(CCCCBr)C2O1]

The general procedure B was followed using (3-(4-bromobutyl)-1H-indene) 1d (100 mg, 0.52 mmol) as a substrate procured 2d (107 mg, 77%) as a brown liquid; R$_f$ 0.3 (5% ethyl acetate/pet. ether); IR (CHCl$_3$)v: 2984, 2931, 1606, 1456, 1371, 1248, 1208, 1049, 867, 753 cm$^{-1}$; $^1$H NMR (400 MHz, CDCl$_3$): δ=1.21 (s, 3H), 1.41 (s, 3H), 1.48-1.52 (m, 1H), 1.54-1.60 (m, 2H), 1.63-1.68 (m, 1H), 1.86-1.93 (m, 2H), 3.28 (dd, J=5.4, 8.8 Hz, 1H), 3.42 (t, J=6.8 Hz, 2H), 4.63 (dd, J=1.1, 5.6 Hz, 1H), 5.57 (d, J=5.6 Hz, 1H), 7.21 (d, J=7.3 Hz, 1H), 7.28 (dd, J=1.4, 7.3 Hz, 1H), 7.32 (dt, J=1.3, 7.3 Hz, 1H) 7.42 (d, J=7.3 Hz, 1H); $^{13}$C-NMR (100 MHz, CDCl$_3$): δ=25.9 (CH$_2$), 26.0 (CH$_3$), 27.5 (CH$_3$), 32.7 (CH$_2$), 33.4 (CH$_2$), 33.8 (CH$_2$), 50.1 (CH), 83.2 (CH), 85.4 (CH), 111.0 (C), 125.1 (CH), 125.8 (CH), 127.6 (CH), 129.1 (CH), 141.0 (C), 144.9 (C). (C$_{16}$H$_{21}$BrO$_2$)

8-benzyl-2,2-dimethyl-8,8a-dihydro-3aH-indeno[1,2-d][1,3]dioxole (2e)

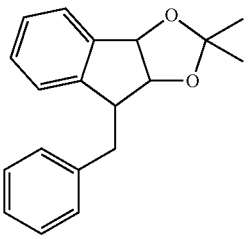 [SMILES: CC1(C)OC2c3ccccc3C(Cc3ccccc3)C2O1]

The general procedure B was followed using (1-benzyl-1H-indene) 1e (100 mg, 0.48 mmol) as a substrate procured 2e (134 mg, 77%) as a colourless liquid; R$_f$ 0.3 (5% ethyl acetate/pet. ether); IR (CHCl$_3$)v: 3027, 2985, 2925, 1603, 1454, 1370, 1210, 1059, 866, 753 cm$^{-1}$; $^1$H NMR (400 MHz, CDCl$_3$): δ=1.15 (s, 3H), 1.36 (s, 3H), 2.88 (d, J=7.5 Hz, 2H), 3.68 (t, J=7.5 Hz, 1H), 4.67 (d, J=5.4 Hz, 1H), 5.41 (d, J=5.4 Hz, 1H), 6.97 (dd, J=1.8, 6.6 Hz, 1H), 7.11 (dd, J=1.5, 7.8 Hz, 2H), 7.21-7.25 (m, 3H), 7.26-7.29 (m, 2H), 7.39 (dd, J=2.1, 7.1 Hz, 1H); $^{13}$C-NMR (100 MHz, CDCl$_3$): δ=26.1 (CH$_3$), 27.5 (CH$_3$), 40.8 (CH$_2$), 50.9 (CH), 83.0 (CH), 84.5 (CH), 110.7 (C), 125.4 (CH), 125.6 (CH), 126.3 (CH), 127.7 (CH), 128.4 (2CH), 128.7 (CH), 129.2 (2CH), 139.0 (C), 141.6 (C), 144.2 (C). (C$_{12}$H$_{20}$O$_2$)

3a-benzyl-2,2-dimethyl-8,8a-dihydro-3aH-indeno[1,2-d][1,3]dioxole (2f)

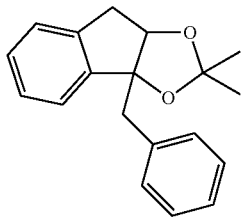 [SMILES: CC1(C)OC2Cc3ccccc3C2(Cc2ccccc2)O1]

The general procedure B was followed using (3-benzyl-1H-indene) 1f (100 mg, 0.48 mmol) as a substrate procured 2f (102 mg, 75%) as a white solid; R$_f$ 0.3 (5% ethyl acetate/pet. ether); mp: 77-79° C.; IR (CHCl$_3$)v: 3066, 3017, 2988, 1604, 1454, 1380, 1216, 1056, 756 cm$^{-1}$; $^1$H NMR (500 MHz, CDCl$_3$): δ=1.05 (s, 3H), 1.22 (s, 3H), 2.65 (dd, J=4.8, 17.2 Hz, 1H), 2.95 (d, J=17.2 Hz, 1H), 3.11 (d, J=13.7 Hz, 1H), 3.23 (d, J=13.8 Hz, 1H), 4.59 (d, J=4.8 Hz, 1H), 7.04 (dd, J=3.7, 7.4 Hz, 2H), 7.11 (dd, J=3.8, 5.5 Hz, 1H), 7.17-7.20 (m, 3H), 7.23-7.25 (m, 2H), 7.32 (dd, J=2.3, 5.5 Hz, 1H); $^{13}$C-NMR (125 MHz, CDCl$_3$): δ=27.2 (CH3), 27.8 (CH$_3$), 36.4 (CH$_2$), 43.7 (CH$_2$), 82.8 (CH), 93.4 (C), 110.3 (C), 124.3 (CH), 125.3 (CH), 126.5 (CH), 127.1 (CH), 127.8 (2CH), 128.5 (CH), 130.5 (2CH), 136.1 (C), 140.3 (C), 145.1 (C). (C$_{19}$H$_{20}$O$_2$)

3a-isopropyl-2,2-dimethyl-8,8a-dihydro-3aH-indeno[1,2-d][1,3]dioxole (2g)

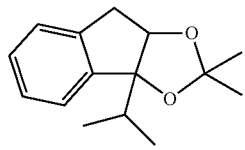 [SMILES: CC(C)C12OC(C)(C)OC1Cc1ccccc12]

The general procedure B was followed using (3-isopropyl-1H-indene) 1g (100 mg, 0.52 mmol) as a substrate procured 2g (87 mg, 63%) as a colourless liquid; $R_f$ 0.3 (5% ethyl acetate/pet. ether); IR (CHCl$_3$)v: 3025, 2962, 2933, 1606, 1471, 1378, 1368, 1243, 1219, 1165, 1094, 1059, 907, 849, 751 cm$^{-1}$; $^1$H NMR (500 MHz, CDCl$_3$): δ=0.81 (d, J=7.0 Hz, 3H), 0.99 (d, J=7.0 Hz, 6H), 1.41 (s, 3H), 2.29 (pent, J=7.0 Hz, 13.8 Hz, 1H), 3.04 (d, J=4.0 Hz, 2H), 4.63 (dd, J=1.6, 4.0 Hz, 1H), 7.20 (d, J=6.8 Hz, 1H), 7.22-7.28 (m, 2H), 7.34 (d, 6.9 Hz, 1H); $^{13}$C-NMR (125 MHz, CDCl$_3$): δ=17.4 (CH$_3$), 17.5 (CH$_3$), 27.6 (CH$_3$), 28 (CH$_3$), 34.5 (CH), 38.3 (CH$_2$), 81.7 (CH), 96.9 (C), 110.1 (C), 124.6 (CH), 125.2 (CH), 127 (CH), 128.4 (CH), 140.8 (C), 144.5 (C). (C$_{15}$H$_{20}$O$_2$)

3a-cyclohexyl 2,2 dimethyl-8,8a-dihydro-3aH-indeno[2,1-d][1,3]dioxole (2h)

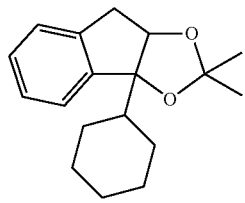 [SMILES: CC1(C)OC2Cc3ccccc3C2(C2CCCCC2)O1]

The general procedure B was followed using (3-cyclohexyl-1H-indene) 1h (100 mg, 0.50 mmol) as a substrate procured 2h (89 mg, 65%) as a colourless liquid; $R_f$ 0.3 (5% ethyl acetate/pet. ether); IR (CHCl$_3$)v: 3070, 2984, 2928, 1732, 1605, 1451, 1377, 1367, 1244, 1175, 1058, 848, 752 cm$^{-1}$; $^1$H NMR (500 MHz, CDCl$_3$): δ=0.92-0.97 (m, 2H), 0.99 (s, 3H), 1.07-1.15 (m, 2H), 1.24-1.28 (m, 2H), 1.40 (s, 3H), 1.66 (d, J=9.7 Hz, 2H), 1.79 (d, J=13.4 Hz, 1H), 1.93 (tt, J=3.0, 12.1 Hz, 1H), 2.04 (d, J=12.9 Hz, 1H), 3.0 (d, J=3.9 Hz, 2H), 4.86 (dd, J=1.8, 3.3 Hz, 1H), 7.19 (dd, J=2.2, 7.1 Hz, 1H), 7.24-7.27 (m, 2H), 7.34 (dd, J=2.2, 7.1 Hz, 1H) $^{13}$C-NMR (125 MHz, CDCl$_3$): δ=26.2 (CH$_2$), 26.4 (2CH$_2$), 27.5 (CH$_2$), 27.6 (2CH$_2$), 28.1 (CH$_3$), 38.1 (CH$_2$), 44.6 (CH), 81.9 (CH), 96.5 (CH), 110.0 (C), 124.6 (CH), 125.1 (CH), 127.0 (CH), 128.3 (CH), 140.8 (C), 144.9 (C). C$_{18}$H$_{24}$O$_2$

2,2-dimethyl-3a-phenyl-8,8a-dihydro-3aH-indeno[1,2-d][1,3]dioxole (2i)

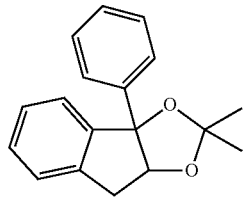 [SMILES: CC1(C)OC2Cc3ccccc3C2(c2ccccc2)O1]

The general procedure B was followed using (3-phenyl-1H-indene) 1i (100 mg, 0.52 mmol) as a substrate procured 2i (85 mg, 82%) as a white solid; $R_f$ 0.3 (5% ethyl acetate/pet. ether); mp: 58-59° C.; IR (CHCl$_3$)v: 3018, 2932, 1601, 1447, 1372, 1216, 1053, 851, 755 cm$^{-1}$; $^1$H NMR (400 MHz, CDCl$_3$): δ=1.24 (s, 3H), 1.54 (s, 3H), 3.19 (d, J=17.3 Hz, 1H), 3.28 (dd, J=4.6, 17.3 Hz, 1H), 4.70 (d, J=4.6 Hz, 1H), 7.20-7.25 (m, 5H), 7.27-7.33 (m, 4H); $^{13}$C-NMR (100 MHz, CDCl$_3$): δ=26.9 (CH$_3$), 27.7 (CH$_3$), 36.8 (CH$_2$), 87.3 (CH), 95.2 (C), 111.0 (C), 125.2 (CH), 125.5 (3CH), 127.3 (CH), 127.7 (CH), 128.3 (2CH), 128.6 (CH), 140.6 (C), 142.4 (C), 145.7 (C). (C$_{18}$H$_{18}$O$_2$)

7-(2,2-dimethyl-8,8a-dihydro-3aH-indeno[2,1-d][1,3]dioxol-3a-yl)heptan-2-one (2j)

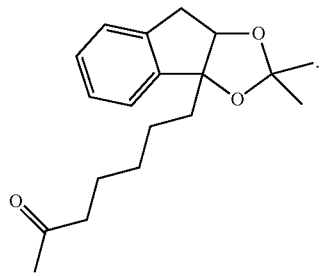 [SMILES: CC(=O)CCCCCC12OC(C)(C)OC1Cc1ccccc12]

The general procedure B was followed using (7-(1H-inden-3-yl)heptan-2-one) 1j (100 mg, 0.44 mmol) as a substrate procured 2j (93 mg, 72%) as a colourless liquid; $R_f$ 0.3 (10% ethyl acetate/pet. ether); IR (CHCl$_3$)v: 3024, 2985, 2934, 1716, 1459, 1368, 1245, 1220, 1055, 1017, 853, 754 cm$^{-1}$; $^1$H NMR (500 MHz, CDCl$_3$): δ=1.04 (s, 3H), 1.10-1.19 (m, 1H), 1.23-1.31 (m, 2H), 1.34-1.39 (m, 1H), 1.41 (s, 3H), 1.49-1.57 (m, 2H), 1.79-1.94 (m, 2H), 2.10 (s, 3H), 2.39 (t, J=7.2 Hz, 2H), 3.06 (d, J=3.0 Hz, 2H), 4.59 (t, J=2.6 Hz, 1H), 7.20 (dd, J=2.9, 7.0 Hz, 1H), 7.26 (dd, J=2.6, 6.7 Hz, 2H), 7.34 (dd, J=2.9, 7.0 Hz, 11H); $^{13}$C-NMR (100 MHz, CDCl$_3$): δ=23.5 (CH$_2$), 23.9 (CH$_2$), 27.4 (CH$_3$), 27.8 (CH$_3$), 29.4 (CH$_2$), 29.8 (CH$_3$), 37.1 (CH$_2$), 37.4 (CH$_2$), 43.5 (CH$_2$), 83.5 (CH), 93.6 (C), 110.0 (C), 124.1 (CH), 125.3 (CH), 127.1 (CH), 128.4 (CH), 140.0 (C), 145.2 (C), 209.1 (C). C$_{19}$H$_{26}$O$_3$

2',2'-dimethyl-3a',8a'-dihydrospiro[cyclopentane-1,8'-indeno[2,1-d][1,3]dioxole](2k)

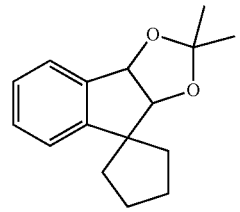 [SMILES: CC1(C)OC2c3ccccc3C3(CCCC3)C2O1]

The general procedure B was followed using (spiro[cyclopentane-1,1'-indene]) 1k (100 mg, 0.2 mmol) as a substrate procured 2k (101 mg, 73%) as a colourless liquid; $R_f$ 0.3 (5% ethyl acetate/pet. ether); IR (CHCl$_3$)v: 2933, 1746, 1606, 1455, 1369, 1242, 1155, 1073, 756 cm$^{-1}$; $^1$H NMR (400 MHz, CDCl$_3$): δ=1.13 (s, 3H), 1.41 (s, 3H), 1.54-1.59

(m, 2H), 1.62-1.69 (m, 1H), 1.72-1.78 (m, 1H), 1.83-1.87 (m, 4H), 4.46 (d, J=5.3 Hz, 1H), 5.58 (d, J=5.3 Hz, 1H), 7.18 (d, J=7.6 Hz, 1H), 7.25 (t, J=7.5 Hz, 1H), 7.32 (t, J=7.5 Hz, 1H), 7.38 (d, J=7.6 Hz, 1H); $^{13}$C-NMR (100 MHz, CDCl$_3$): δ=25.2 (CH$_2$), 25.4 (CH$_2$), 26.5 (CH$_3$), 27.6 (CH$_3$), 33.5 (CH$_2$), 41.7 (CH$_2$), 57.1 (C), 82.6 (CH), 87.6 (CH), 111.2 (C), 123.0 (CH), 125.2 (CH), 127.2 (CH), 129.0 (CH), 141.0 (C), 149.2 (C). C$_{16}$H$_{20}$O$_2$ 3a-(but-3-enyl)-2,2-dimethyl-8,8a-dihydro-3aH-indeno[2,1-d][1,3]dioxole (2m)

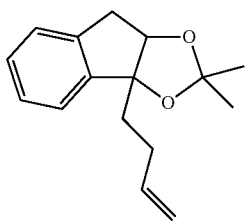 [SMILES: C=CCCC12OC(C)(C)OC1Cc1ccccc12]

The general procedure B was followed using (3-(but-3-en-1-yl)-1H-indene) 1m (100 mg, 0.59 mmol) as a substrate procured 2m (105 mg, 73%) as a colourless liquid; R$_f$ 0.3 (8% ethyl acetate/pet. ether); IR (CHCl$_3$)ν: 3074, 2984, 2931, 1641, 1607, 1459, 1369, 1245, 1166, 1058, 911, 761 cm$^{-1}$; $^1$H NMR (500 MHz, CDCl$_3$): δ=1.05 (s, 3H), 1.42 (s, 3H), 1.90-1.94 (m, 1H), 1.95-1.97 (m, 1H), 2.00-2.05 (m, 1H), 2.11-2.19 (m, 1H), 3.08 (d, J=2.6 Hz, 2H), 4.63 (t, J=2.6 Hz, 1H), 4.94 (dd, J=1.7, 10.1 Hz, 1H), 5.01 (dd, J=1.7, 17.1 Hz, 1H), 5.82 (m, 1H), 7.19-7.22 (m, 1H), 7.24-7.28 (m, 2H), 7.33-7.35 (m, 1H); $^{13}$C-NMR (125 MHz, CDCl$_3$): δ=27.5 (CH$_3$), 27.8 (CH$_3$), 28.5 (CH$_2$), 36.6 (CH$_2$), 37.1 (CH$_2$), 83.4 (CH), 93.5 (C), 110.2 (C), 114.6 (CH$_2$), 124.2 (CH), 125.4 (CH), 127.2 (CH), 128.5 (CH), 138.0 (C), 140.1 (C), 145.1 (C). (C$_{16}$H$_{20}$O$_2$), 2,2,9b-Trimethyl-3a,4,5,9b-tetrahydronaphtho[2,1-d][1,3]dioxole (2o)

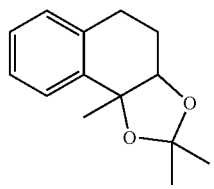 [SMILES: CC1(C)OC2CCc3ccccc3C2(C)O1]

The general, procedure B was followed using 4-methyl-1,2-dihydronaphthalene (1o) (100 mg, 0.69 mmol) as a substrate procured 2o (99 mg, 65%) as a colorless liquid; R$_f$ 0.3 (5% ethyl acetate/pet. ether); IR (CHCl$_3$)ν: 3022, 2982, 2870, 1492, 1439, 1367, 1255, 123.7, 1107, 1090, 1001, 847, 762 cm$^{-1}$; $^1$H NMR (400 MHz, CDCl$_3$): δ=0.96 (s, 3H), 1.42 (s, 3H), 1.57 (s, 3H), 1.90-1.98 (m, 1H), 2.21-2.28 (m, 1H), 2.64 (m, 1H), 3.04 (ddt, J=4.5, 5.3 Hz, 1H), 4.17 (dd, J=1.4, 7.7 Hz, 1H), 7.06 (d, J=1.4, 7.5 Hz, 1H), 7.17 (dt, J=1.4, 7.3 Hz, 1H), 7.22 (t, J=7.6 Hz, 1H), 7.48 (d, J=7.5 Hz, 1H); $^{13}$C-NMR (100 MHz, CDCl$_3$): δ=23.7 (CH$_3$), 24.1 (CH$_2$), 27.1 (CH$_3$), 27.3 (CH$_3$), 25.6 (CH$_3$), 79.0 (CH), 79.1 (C), 108.0 (C), 126.5 (CH), 126.9 (CH), 127.8 (CH), 127.9 (CH), 135.0 (C), 140.2 (C) ppm; HRMS (ESI+): calcd. for C$_{14}$H$_{18}$O$_2$Na$^+$ 241.1199. found 241.1199.

7-Methoxy-2,2,9b-trimethyl-3a,4,5,9b-tetrahydronaphtho[1,2-d]1,3dioxole (2p)

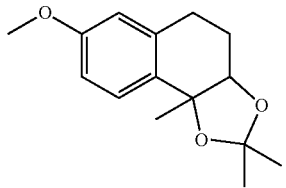

The general procedure B was followed using 7-methoxy-4-methyl-1,2-dihydronaphthalene (1p) (100 mg, 0.57 mmol) as a substrate procured 2p (101 mg, 71%) as a colorless liquid; R$_f$ 0.3 (10% ethyl acetate/pet. ether); $^1$H NMR (500 MHz, CDCl$_3$): δ=0.97 (s, 3H), 1.41 (s, 3H), 1.54 (s, 3H), 1.94 (td, J=5.0, 13.4 Hz, 1H), 2.25 (d, J=13.4 Hz, 1H), 2.58 (dd, J=5.0, 16.4 Hz, 1H), 3.06 (ddt, J=5.0, 12.2 Hz, 1H), 3.77 (s, 3H), 4.13 (m, 1H), 6.56 (s, 1H), 6.79 (d, J=8.5 Hz, 1H), 7.30 (d, J=8.5 Hz 1H); $^{13}$C-NMR (125 MHz, CDCl$_3$): δ=24.1 (CH$_2$), 24.3 (CH$_2$), 27.3 (3CH$_3$), 55.12 (CH$_3$), 79.0 (C), 79.1 (CH), 107.8 (C), 112.0 (CH), 113.1 (CH), 129.1 (CH), 132.7 (C), 136.5 (C), 158.3 (C) ppm; GC-HRMS (+EI): calcd. for C$_{15}$H$_{20}$O$_3^+$ 248.1407. found 248.1425.

2,2-Dimethyl-9b-phenyl-3a,4,5,9btetrahydronaphtho[2,1-d][1,3]dioxole (2q)

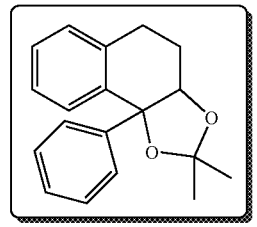

The general procedure B was followed using 4-phenyl-1,2-dihydronaphthalene (1q) (100 mg, 0.49 mmol) as a substrate procured 2q (82 mg, 60%) as a colorless solid; R$_f$ 0.3 (5% ethyl acetate/pet. ether); mp: 95-97° C.; $^1$H NMR (400 MHz, CDCl$_3$): δ=1.13 (s, 3H), 1.60 (s, 3H), 2.05 (ddt, J=1.6, 5.2, 13.6 Hz, 1H), 2.17-2.24 (m, 1H), 2.75 (dd, J=4.9, 16.1 Hz, 1H), 3.20 (dt, J=5.2, 12.4 Hz, 1H), 4.19 (d, J=4.9 Hz, 1H), 7.08 (d, J=7.5 Hz, 1H), 7.15 (d, J=6.8 Hz, 2H), 7.19 (d, J=6.8 Hz, 1H), 7.24-7.28 (m, 1H), 7.29-7.30 (m, 4H); $^{13}$C-NMR (100 MHz, CDCl$_3$): δ=22.9 (CH$_2$), 23.4 (CH2), 27.0 (CH$_3$), 27.5 (CH$_3$), 80.5 (CH), 83.9 (C), 108.7 (C), 126.6 (3CH), 127.1 (CH), 127.2 (CH), 127.7 (CH), 127.9 (2CH), 130.5 (CH), 136.1 (C), 139.3 (C), 144.5 (C) ppm; HRMS (ESI+): calcd. for C$_{19}$H$_{20}$O$_2$Na$^+$ 303.1356. found 303.1353.

7-Methoxy-2,2-dimethyl-9b-phenyl-3a,4,5,9b-tetrahydronaphtho[1,2-d][1,3] dioxole (2r)

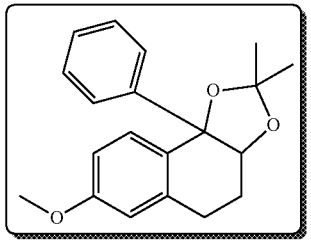

The general procedure B was followed using 7-methoxy-4-phenyl-1,2-dihydronaphthalene (1r) (100 mg, 0.42 mmol) as a substrate procured 2r (84 mg, 64%) as a white solid; $R_f$ 0.3 (15% ethyl acetate/pet. ether); $H^1$ NMR (500 MHz) δ: 1.14 (s, 3H), 1.59 (s, 3H), 2.21 (ddd, J=5.1, 13.2 Hz, 1H), 2.20 (d, J=14.2 Hz, 1H), 2.58 (dd, J=5.0, 16.8 Hz, 1H), 3.06 (ddd, J=5.5, 13.3 Hz, 1H), 3.79 (s, 3H), 4.17 (s, 1H), 6.56 (s, 1H), 6.69 (dd, J=2.2, 8.2 Hz, 1H), 6.98 (d, J=2.2 Hz, 1H), 7.2-7.3 (m, 1H), 7.27-7.30 (m, 4H); $^{13}C$ NMR (125 MHz) δ: 23.1 ($CH_2$), 23.8 ($CH_2$), 27.1 ($CH_3$), 27.5 ($CH_3$), 55.8 ($CH_3$), 80.5 (CH), 83.5 (C), 108.6 (C), 111.5 (CH), 113.4 (CH), 126.6 (2CH), 127.1 (CH), 127.9 (2CH), 131.7 (CH), 137.5 (2C), 144.7 (C), 158.4 (C) ppm; HRMS (ESI+): calcd. for $C_{20}H_{22}O_3Na^+$ 333.1461. found 333.1458.

2-(2-benzoylphenyl)-2-methyl-1-phenylpropan-1-one (5)

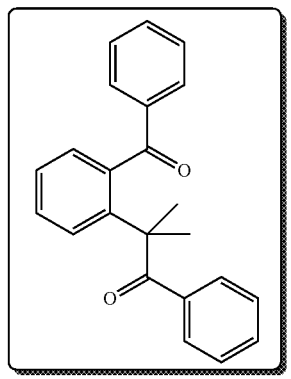

The general procedure B was followed using (1,1-dimethyl-2,3-diphenyl-1H-indene) 1l (100 mg, 0.34 mmol) as a substrate procured 5 (14 mg, 13%) as a colourless liquid; $R_f$ 0.3 (10% ethyl acetate/pet. ether); IR ($CHCl_3$)ν: 3025, 2962, 2933, 1606, 1716, 1685, 1368, 1243, 1219, 1165, 1094, 1059, 907, 849, 751 $cm^{-1}$; $^1H$ NMR (400 MHz, $CDCl_3$): δ −1.66 (s, 6H), 7.16 (t, J=8.0 Hz, 2H), 7.23 (dd, J=1.3, 7.5 Hz, 1H), 7.27-7.33 (m, 4H), 7.50 (t, J=7.8 Hz, 1H), 7.51-7.53 (m, 2H), 7.55-7.58 (m, 3H), 7.63 (d, J=7.78 Hz, 1H); $^{13}C$-NMR (100 MHz, $CDCl_3$): δ=29.0 (2$CH_3$), 51.68 (C), 125.7 (CH), 127.4 (CH), 127.8 (2CH), 128.11 (2CH), 129.8 (2CH), 130.1 (CH), 130.3 (2CH), 130.7 (CH), 131.5 (CH), 132.9 (CH), 136.1 (C), 137.2 (C), 137.5 (C), 144.9 (C), 197.8 (C), 202.1 (C). ($C_{23}H_{20}O_2$).

2,2-dimethyl-3a-(2-(oxiran-2-yl)ethyl)-3a,8a-dihydro-8H-indeno[1,2-d][1,3]dioxole (6)

Diastereomeric Mixture with 50:50 Percent

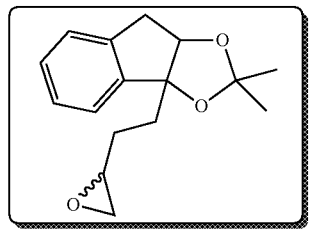

The general procedure B was followed using (3a-(but-3-enyl)-2,2-dimethyl-8,8a-dihydro-3aH-indeno[2,1-d][1,3]dioxole) 2m (110 mg, 0.54 mmol) as a substrate procured 6 (110 mg, 79%) as a colourless liquid; $R_f$ 0.5 (20% ethyl acetate/pet. ether); IR ($CHCl_3$)ν: 3074, 2984, 2931, 1641, 1607, 1459, 1369, 1245, 1166, 1058, 911, 761 $cm^{-1}$; $^1H$ NMR (500 MHz, $CDCl_3$): δ=1.03 (s, 1.5H), 1.04 (s, 1.5H), 1.40 (s, 1.5H), 1.41 (s, 1.5H), 1.42-1.46 (m, 0.5H), 1.46-1.50 (m, 0.5H), 1.57-1.64 (m, 0.5H), 1.71-1.78 (m, 0.5H), 1.93-2.00 (m, 1H), 2.00-2.12 (m, 1H), 2.41 (dd, J=2.7, 4.9 Hz, 0.5H), 2.48 (dd, J=2.7, 4.9 Hz, 0.5H), 2.71 (t, J=4.4 Hz, 0.5H), 2.74 (t, J=4.4 Hz, 0.5H), 2.88-2.92 (m, 1H), 3.03-3.07 (m, 1H), 3.07-3.10 (m, 1H), 4.58-4.59 (m, 1H), 7.19-7.21 (m, 1H), 7.23-7.25 (m, 1H), 7.25-7.28 (m, 1H), 7.32-7.33 (m, 0.5H), 7.33-7.35 (m, 0.5H); $^{13}C$-NMR (125 MHz, $CDCl_3$): δ=27.3 (CH2), 27.4 ($CH_2$), 27.5 (2$CH_3$), 27.8 (2$CH_3$), 33.2 ($CH_2$), 33.5 ($CH_2$), 37.0 ($CH_2$), 37.1 ($CH_2$), 47.0 (2$CH_2$), 52.0 (CH), 52.1 (CH), 83.3 (CH), 83.6 (CH), 93.1 (2C), 110.3 (2C), 124.1 (2CH), 125.4 (2CH), 127.3 (2CH), 128.6 (2CH), 139.9 (C), 140.1 (C), 144.7 (C), 144.9 (C). ($C_{16}H_{20}O_3$)

2-methyl-3,4,9,9a-tetrahydro-2H-2,4a-epoxyindeno[2,1-b]pyran (7)

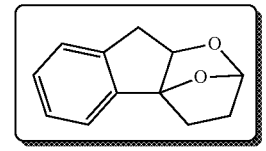

To a solution of 4-(1H-inden-3-yl)butan-2-one 1n (100 mg, 0.54 mmol) in acetonitrile (10 mL) was added ethyl acetate (2 mL), water (2 mL), $NaHCO_3$ (135.3 mg, 1.61 mmol) and the reaction mixture was stirr for 10 min then solid oxone was added (660.1 mg, 1.07 mmol), stirr the reaction mixture at room temperature for 10 h. After completion of the reaction, reaction mixture extracted with water and ethyl acetate (3×50 mL). The organic layer was dried over sodium sulphate and evaporated under reduced pressure. The crude product was purified by silica gel column (ethyl acetate and pet ether as eluent) to afford 7 (80 mg, 74%) as a white solid; $R_f$ 0.3 (5% ethyl acetate/pet. ether); mp: 141-145° C.; IR ($CHCl_3$)ν: 2982, 2935, 1607, 1461, 1381, 1214, 1134, 1082, 1015, 937, 757 $cm^{-1}$; $^1H$ NMR (500 MHz, $CDCl_3$): δ=1.55 (t, J=4.0 Hz, 1H), 1.65 (s, 3H), 2.12 (dt, J=5.0, 8.5 Hz, 1H), 2.25 (dd, J=7.2, 12.1 Hz, 1H), 2.71

(dd, J=10.3, 14.6 Hz, 1H), 3.02 (dd, J=7.2, 15.0 Hz, 1H), 3.15 (dt, J=7.7, 13.1 Hz, 1H), 4.7 (dd, J=7.9, 10.2 Hz, 1H), 7.12-7.16 (m, 2H), 7.17-7.20 (m, 2H); $^{13}$C-NMR (125 MHz, CDCl$_3$): δ=23.4 (CH$_3$), 29.6 (CH$_2$), 37.1 (CH$_2$), 38.3 (CH$_2$), 77.1 (CH), 94.3 (C), 107.9 (C), 122.5 (CH), 124.1 (CH), 124.6 (CH), 127.7 (CH), 136.8 (C), 146.7 (C). C$_{13}$H$_{14}$O$_2$.

(4S,5S)-2,2-Dimethyl4,5-diphenyl-1,3-dioxolane (9a)

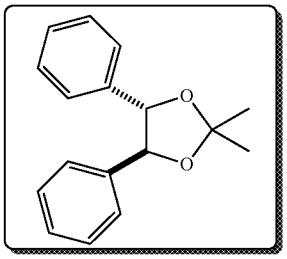

The general procedure B was followed using trans-stilbene (8a) (100 mg, 0.56 mmol) as a substrate procured 9a (62 mg, 44%) as a colorless liquid; R$_f$ 0.3 (5% ethyl acetate/pet. ether); mp: 65-68° C.; $^1$H NMR (400 MHz, CDCl$_3$): δ=1.67 (s, 6H), 4.78 (s, 2H), 7.21-7.23 (m, 3H), 7.30-7.32 (m, 6H), 7.35 (d, J=3.3 Hz, 1H); $^{13}$C-NMR (100 MHz, CDCl$_3$): δ=27.2 (2CH$_3$), 85.4 (2CH), 109.4 (C), 126.7 (4CH), 128.2 (2CH), 128.4 (4CH), 136.7 (2C) ppm.

(4S,5R)-2,2-Dimethyl-4,5-diphenyl-1,3-dioxolane (9b)

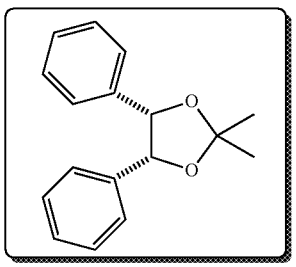

The general procedure B was followed using cis-stilbene (8b) (100 mg, 0.55 mmol) as a substrate procured 9b (51 mg, 36%) as a colorless liquid; R$_f$ 0.3 (5% ethyl acetate/pet. ether); mp: 65-68° C.; $^1$H NMR (400 MHz, CDCl$_3$): δ=1.62 (s, 3H), 1.83 (s, 3H), 5.49 (br.s, 2H), 6.90-7.23 (m, 10H) ppm.

1,3-Dihydro-2H-inden-2-one (4a)

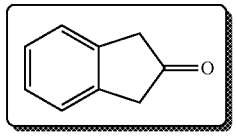

The general procedure C was followed using 1H-indene (1a) (100 mg, 0.86 mmol) as a substrate procured 4a (89 mg, 78%) as a white solid; R$_f$ 0.3 (15% ethyl acetate/pet. ether); H$^1$ NMR (200 MHz): δ=3.57 (s, 4H), 7.26-7.31 (m, 4H) ppm; $^{13}$C NMR (50 MHz): δ=44.1 (2CH$_2$), 125.1 (2CH), 127.4 (2CH), 137.8 (2C), 215.3 (C) ppm.

1-Phenyl-1,3-dihydro-2H-inden-2-one (4d)

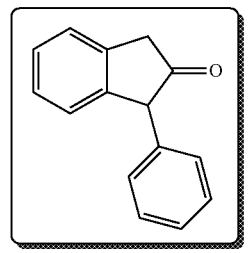

The general procedure C was followed using 3-phenyl-1H-indene (1d) (100 mg, 0.52 mmol) as a substrate procured 4d (66 mg, 61%) as a colorless solid; R$_f$ 0.3 (15% ethyl acetate/pet. ether); H$^1$ NMR (200 MHz): δ=3.62 (s, 2H), 4.63 (s, 1H), 7.04-7.16 (m, 3H), 7.20-7.36 (s, 6H) ppm.

1-Benzyl-1,3-dihydro-2H-inden-2-one (4e)

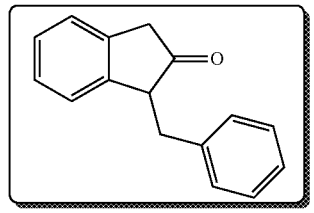

The general procedure C was followed using 3-benzyl-1H-indene (1e) (100 mg, 0.48 mmol) as a substrate procured 4e (81 mg, 75%) as a colorless solid; R$_f$ 0.3 (15% ethyl acetate/pet. ether); H$^1$ NMR (200 MHz): 2.93-3.04 (m, 1H), 3.19-3.54 (m, 3H), 3.74-3.80 (m, 1H), 6.92-6.96 (m, 1H), 7.04-7.09 (m, 2H), 7.16-7.21 (m, 6H) ppm.

3-propyl-1H-indene (4f)

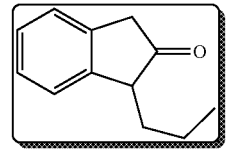

The general procedure C was followed using 3-propyl-1H-indene (1f) (100 mg, 0.63 mmol) as a substrate procured 4f (83 mg, 74%) as a colorless liquid; R$_f$ 0.3 (10% ethyl acetate/pet. ether); H$^1$ NMR (200 MHz): 0.922 (t, J=7.4 Hz, 3H), 1.28-1.42 (m, 2H), 1.81-1.91 (m, 2H), 5.76 (t, J=5.7 Hz, 1H), 3.52 (s, 2H), 7.26-7.31 (m, 4H) ppm.

1-(3-Chloropropyl)-1,3-dihydro-2H-inden-2-one (4g)

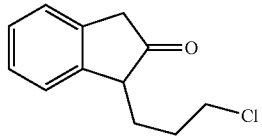 [SMILES: O=C1Cc2ccccc2C1CCCCl]

The general procedure C was followed using 3-(3-chloropropyl)-1H-indene (1g) (100 mg, 0.5 mmol) as a substrate procured 4g (80 mg, 74%) as a yellow liquid; $R_f$ 0.3 (15% ethyl acetate/pet. ether); $H^1$ NMR (500 MHz): δ=1.75-1.90 (m, 2H), 1.94-2.02 (m, 1H), 2.05-2.12 (m, 1H), 3.48-3.59 (m, 5H), 7.26-7.31 (m, 4H); $^{13}C$ NMR (125 MHz): δ=28.7 (CH$_2$), 29.0 (CH$_2$), 43.4 (CH$_2$), 44.8 (CH$_2$), 51.8 (CH), 1 124.4 (CH), 124.9 (CH), 127.5 (CH), 127.6 (CH), 136.8 (C), 140.4 (C), 217.5 (C) ppm; HRMS (ESI+): calcd. for $C_{12}H_{13}OClNa^+$ 231.0547. found 231.0548.

1-(3-Azidopropyl)-1,3-dihydro-2H-inden-2-one (4h)

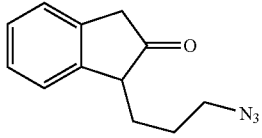 [SMILES: [N-]=[N+]=NCCCC1C(=O)Cc2ccccc21]

The general procedure C was followed using 3-(3-azidopropyl)-1H-indene (1h) (100 mg, 0.50 mmol) as a substrate procured 4h (78 mg, 72%) as a yellow liquid; $R_f$ 0.3 (15% ethyl acetate/pet. ether); $H^1$ NMR (500 MHz): δ=1.57-1.71 (m, 2H), 1.91-1.99 (m, 1H), 2.01-2.09 (m, 1H), 3.12-3.31 (m, 2H), 3.42-3.63 (m, 3H), 7.14-7.56 (m, 4H); $^{13}C$ NMR (125 MHz): δ=25.5 (CH$_2$), 28.3 (CH$_2$), 43.4 (CH$_2$), 51.3 (CH$_2$), 52.2 (CH), 124.4 (CH), 124.9 (CH), 127.6 (2CH), 136.8 (C), 141.3 (C), 217.5 (C) ppm; HRMS (ESI+): calcd. for $C_{12}H_{13}ON_3Na^+$ 238.0951. found 238.0952.

1-Phenyl-3,4-dihydronaphthalen-2(1H)-one (4p)

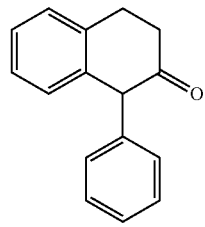 [SMILES: O=C1CCc2ccccc2C1c1ccccc1]

The general procedure C was followed using 4-phenyl-1,2-dihydronaphthalene (1p) (100 mg, 0.49 mmol) as a substrate procured 4p (70 mg, 65%) as a colorless solid, melting point 163-166° C.; $R_f$ 0.3 (15% ethyl acetate/pet. ether); $H^1$ NMR (200 MHz): 2.60-2.68 (m, 1H), 2.73-2.90 (m, 1H), 3.10-3.33 (m, 2H), 4.81 (s, 1H), 7.04-7.49 (m, 9H) ppm.

1-(p-Tolyl)-3,4-dihydronaphthalen-2(1H)-one (4r)

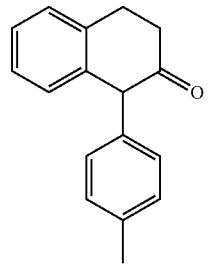 [SMILES: Cc1ccc(C2C(=O)CCc3ccccc32)cc1]

The general procedure C was followed using 4-(p-tolyl)-1,2-dihydronaphthalene (1r) (100 mg, 0.45 mmol) as a substrate procured 4r (65 mg, 61%) as a colorless liquid; $R_f$ 0.3 (15% ethyl acetate/pet. ether); $H^1$ NMR (500 MHz): δ=2.31 (s, 3H), 2.53-2.61 (m, 1H), 2.67-2.75 (m, 1H), 2.98-3.05 (m, 1H), 3.08-3.15 (m, 1H), 4.71 (s, 1H), 6.98 (d, J=8.1 Hz, 2H), 7.01 (d, J=7.6 Hz, 1H), 7.12 (d, J=7.6 Hz, 2H), 7.18-7.24 (m, 1H), 7.27 (d, J=4.4 Hz, 2H); $^{13}C$ NMR (125 MHz): δ=21.0 (CH$_3$), 28.2 (CH$_2$), 37.0 (CH$_2$), 59.5 (CH), 127.2 (CH), 127.3 (CH), 127.4 (CH), 127.9 (2CH), 129.4 (CH), 129.5 (CH), 129.6 (CH), 134.5 (C), 136.7 (C), 137.0 (2C), 209.9 (C) ppm; HRMS (ESI+): calcd. for $C_{17}H_{16}ONa^+$ 259.1093. found 259.1093.

6-Methoxy-1-phenyl-3,4-dihydronaphthalen-2(1H)-one (4s)

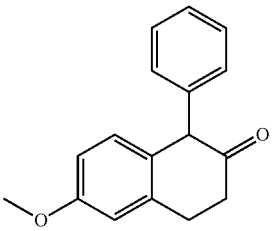 [SMILES: COc1ccc2c(c1)CCC(=O)C2c1ccccc1]

The general procedure C was followed using 7-methoxy-4-phenyl-1,2-dihydronaphthalene (4s) (100 mg, 0.42 mmol) as a substrate procured 4s (77 mg, 72%) as a colorless liquid; $R_f$ 0.3 (15% ethyl acetate/pet. ether); $H^1$ NMR (500 MHz): δ=2.56-2.62 (m, 1H), 2.71-2.77 (m, 1H), 2.98-3.04 (m, 1H), 3.09-3.15 (m, 1H), 3.85 (s, 3H), 4.73 (s, 1H), 6.80-6.84 (m, 2H), 6.96 (d, J=8.6 Hz, 1H), 7.12 (d, J=7.1 Hz, 2H), 7.28 (t, J=6.6 Hz, 1H), 7.33 (t, J=7.1 Hz, 2H); $^{13}C$ NMR (125 MHz): δ=28.4 (CH$_2$), 36.7 (CH$_2$), 55.3 (CH$_3$), 59.0 (CH), 112.8 (CH), 113.1 (CH), 127.1 (CH), 128.4 (C), 128.5 (2CH), 128.6 (2CH), 130.6 (CH), 137.9 (C), 138.2 (C), 158.8 (C), 209.8 (C) ppm; HRMS (ESI+): calcd. for $C_{17}H_{16}O_2Na^+$ 275.1043. found 275.1040.

6-Methoxy-1-(p-tolyl)-3,4-dihydronaphthalen-2(1H)-one (4t)

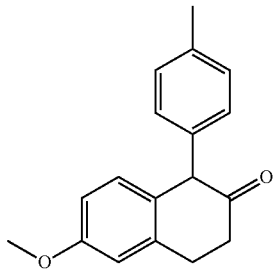 [SMILES: COc1ccc2c(c1)CCC(=O)C2c1ccc(C)cc1]

The general procedure C was followed using 7-methoxy-4-phenyl-1,2-dihydronaphthalene (1t) (100 mg, 0.40 mmol) as a substrate procured 4t (73 mg, 69%) as a colorless liquid; $R_f$ 0.3 (15% ethyl acetate/pet. ether); $H^1$ NMR (500 MHz) δ: 2.31 (s, 3H), 2.51-2.57 (m, 1H), 2.66-2.72 (m, 1H), 2.94-3.00 (m, 1H), 3.04-3.10 (m, 1H), 3.82 (s, 3H), 4.66 (s, 1H), 6.79 (dd, J=2.5, 8.4 Hz, 1H), 6.82 (d, J=2.52 Hz, 1H), 6.93 (d, J=8.16 Hz, 1H), 6.98 (d, J=7.94 Hz, 2H), 7.11 (d, J=8.14 Hz, 2H); $^{13}$C NMR (125 MHz) δ: 21.0 (CH$_3$), 28.4 (CH$_2$), 36.8 (CH$_2$), 55.3 (CH$_3$), 58.7 (CH), 112.8 (CH), 113.1 (CH), 128.4 (2CH), 128.6 (C), 129.4 (2CH), 130.6 (CH), 134.9 (C), 136.8 (C), 138.1 (C), 158.7 (C), 209.9 (C) ppm; HRMS (ESI+): calcd. for $C_{18}H_{18}O_2Na^+$ 289.1199. found 289.1199.

1-Allyl-1,3-dihydro-2H-inden-2-one (4u)[8]

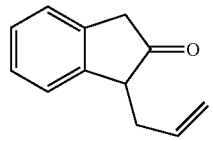

The general procedure C was followed using 3-allyl-1H-indene (1u) (100 mg, 0.64 mmol) as a substrate procured 4s (76 mg, 69%) as a colorless liquid; $R_f$ 0.3 (15% ethyl acetate/pet. ether); NMR (200 MHz): δ=2.51-2.78 (m, 2H), 3.49-3.57 (m, 3H), 4.98-5.11 (m, 2H), 5.61-5.82 (m, 1H), 7.26-7.35 (m, 4H); $^{13}$C NMR (50 MHz): δ=35.7 (CH$_2$), 43.4 (CH$_2$), 52.6 (CH), 117.8 (CH$_2$), 124.8 (2CH), 127.4 (CH), 127.5 (CH), 134.4 (CH), 136.8 (C), 141.5 (C), 217.1 (C) ppm.

Advantages of the Invention i. One step process at ambient temperature and pressure.
ii. Library of compounds generated by the process.
iii. Utility of the substituted compounds of library for anti-HIV, anti-cancer and anti-malarial.
iv. One of the substituted compounds has utility as ligand for many other industrial applications.

We claim:

1. A simple, one step, stereospecific, oxone-acetone mediated, metal free process for preparation of a compound of Formula (I),

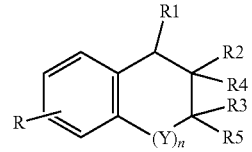

Formula (I)

wherein,
R2 and R3 together represent dioxolo

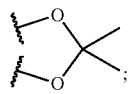

and R1, or R4, or R5 that do not form the dioxolo group are independently selected from the group consisting of hydrogen, alkoxy, unsubstituted or substituted phenyl, halogen, hydroxy, nitro, amino, carbonyl, —COOH, cyano, azo, unsubstituted or substituted benzyl group, C1 to C6 cyclo rings optionally having one or more heteroatoms selected from N, O or S, heteroaryl, unsubstituted linear or branched alkyl radical having 2 to 10 C atoms, substituted linear or branched alkyl radical having 2 to 10 C atoms, in which one or more CH2 groups optionally each independently of one another be replaced by —C=O, —N—, —O—, —S—, —CH=CH—, or —C≡C—, unsubstituted linear or branched alkenyl radical having 2 to 10 C atoms, substituted linear or branched alkenyl radical having 2 to 10 C atoms, unsubstituted linear or branched alkynyl radical having 2 to 10 C atoms, and substituted linear or branched alkynyl radical having 2 to 10 C atoms;

Y is —CHR6, or heteroatom; wherein R6 is selected from hydrogen, methyl, and phenyl;
R is hydrogen or alkoxy; and
n is 0 or 1; with the proviso when n=0, Formula I forms five membered ring or three carbon chain, or when n=1, Formula I forms six membered ring; said process comprising:
(i) mixing compound of Formula (II):

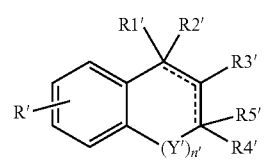

Formula (II)

wherein,
R1', or R3', or R5' are independently selected from the group consisting of hydrogen, alkoxy, unsubstituted or substituted phenyl, halogen, hydroxy, nitro, amino, carbonyl, —COOH, cyano, azo, unsubstituted or substituted benzyl group, C1 to C6 cyclo rings which optionally having one or more heteroatoms selected from N, O or S, heteroaryl, unsubstituted linear or branched alkyl radical having 2 to 10 C atoms, substituted linear or branched alkyl radical having 2 to 10 C atoms, in which one or more CH2 groups optionally each independently of one another be replaced by —C=O, —N—, —O—, —S—, —CH=CH—, or —C≡C—, unsubstituted linear or branched alkenyl radical having 2 to 10 C atoms, substituted linear or branched alkenyl radical having 2 to 10 C atoms; unsubstituted linear or branched alkynyl radical having 2 to 10 C atoms and substituted linear or branched alkynyl radical having 2 to 10 C atoms;

R2' is hydrogen;

R4' is none;

Y' is —CHR6', or heteroatom; wherein R6' is selected from hydrogen, methyl, and phenyl;

R' is hydrogen or alkoxy;

n' is 0 or 1; with the proviso when n'=0, Formula II forms five membered ring or three carbon chain, or when n'=1, Formula II forms six membered ring; and '. . .' between CR1 'R2' and CR3' represents a single bond, and '. . .' between CR3' and CR4R5' represents a double bond;

with powdered Oxone ($H_3K_5S_4O_{18}$) and sodium bicarbonate ($NaHCO_3$) in a ratio in a range of 2:3 in a mixture of acetone, ethyl acetate, and water to obtain a reaction mixture;

(ii) stirring the reaction mixture obtained in step (i) at room temperature in a range of 25 to 30° C. for a period in a range of 2-5 hours; and (iii) evaporating excess acetone under reduced pressure after completion of reaction, portioning the remaining reaction mixture between water and ethyl acetate and followed by purification to obtain compound of Formula I.

2. The process as claimed in claim 1, wherein the mixture of acetone, ethyl acetate, and water is in a ratio of 5:1:1.

3. The process as claimed in claim 1, wherein the compound of Formula I has the structure of Formula (VI):

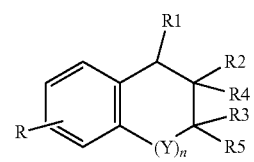

(VI)

wherein R' is selected from hydrogen, alkoxy, phenyl which is unsubstituted or substituted, halogen, hydroxy, nitro, amino, carbonyl, —COOH, cyano, azo, benzyl group which is unsubstituted or substituted; C1 to C6 cyclo rings which may have one or more heteroatoms selected from N, O or S; a heteroaryl; a linear or branched alkyl radical having 2 to 10 C atoms which is unsubstituted or substituted; in which one or more CH2 groups may each, independently of one another, be replaced by —C═O—, —N—, —O—, —S—, or —CH═CH—; a linear or branched alkenyl radical having 2 to 10 C atoms which is unsubstituted or substituted; and a linear or branched alkynyl radical having 2 to 10 C atoms which is unsubstituted or substituted.

4. The process as claimed in claim 1, wherein the compound of Formula I is selected from the group consisting of:

(i) 2,2-dimethyl-8,8a-dihydro-3aH-indeno[1,2-d][1,3]dioxole (2a);

(ii) 2,2-dimethyl-3a-propyl-8,8a-dihydro-3aH-indeno[1,2-d][1,3]dioxole (2b);

(iii) 3a-(3-chloropropyl)-2,2-dimethyl-8,8a-dihydro-3aH-indeno[1,2-d][1,3]dioxole (2c);

(iv) 8-(4-bromobutyl)-2,2-dimethyl-8,8a-dihydro-3aH-indeno[1,2-d][1,3]dioxole (2d);

(v) 8-benzyl-2,2-dimethyl-8,8a-dihydro-3aH-indeno[1,2-d][1,3]dioxole (2e);

(vi) 3a-benzyl-2,2-dimethyl-8,8a-dihydro-3aH-indeno[1,2-d][1,3]dioxole (2f);

(vii) 3a-isopropyl-2,2-dimethyl-8,8a-dihydro-3aH-indeno[1,2-d][1,3]dioxole (2g);

(viii) 3a-cyclohexyl-2,2-dimethyl-8,8a-dihydro-3aH-indeno[2,1-d][1,3]dioxole (2h);

(ix) 2,2-dimethyl-3a-phenyl-8,8a-dihydro-3aH-indeno[1,2-d][1,3]dioxole (2i);

(x) 7-(2,2-dimethyl-8,8a-dihydro-3aH-indeno[2,1-d][1,3]dioxol-3a-yl)heptan-2-one (2j);

(xi) 3a-(but-3-enyl)-2,2-dimethyl-8,8a-dihydro-3aH-indeno[2,1-d][1,3]dioxole (2m); and (xii) 2,2-dimethyl-3a-(2-(oxiran-2-yl)ethyl)-3a,8a-dihydro-8H-indeno[1,2-d][1,3]dioxole (6).

5. A simple, one step, stereospecific, oxone-acetone mediated, metal free process for preparation of a compound of Formula (I),

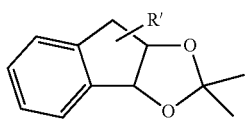

Formula (I)

wherein,

R2 is hydrogen and R1, R3 and R4 that do not form the dioxolo group are independently selected from the group consisting of hydrogen, alkoxy, unsubstituted or substituted phenyl, halogen, hydroxy, nitro, amino, carbonyl, —COOH, cyano, azo, unsubstituted or substituted benzyl group, C1 to C6 cyclo rings optionally having one or more heteroatoms selected from N, O or S, heteroaryl, unsubstituted linear or branched alkyl radical having 2 to 10 C atoms, substituted linear or branched alkyl radical having 2 to 10 C atoms, in which one or more CH2 groups optionally each independently of one another be replaced by —C═O, —N—, —O—, —S—, —CH═CH—, or —C≡C—, unsubstituted linear or branched alkenyl radical having 2 to 10 C atoms, substituted linear or branched alkenyl radical having 2 to 10 C atoms, unsubstituted linear or branched alkynyl radical having 2 to 10 C atoms, and substituted linear or branched alkynyl radical having 2 to 10 C atoms;

Y is —CHR6; wherein R6 is selected from hydrogen, methyl, and phenyl, and wherein R5 together with CH of CHR6 represent dioxolo

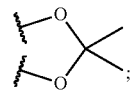

R is hydrogen or alkoxy; and n is 1, Formula I forms six membered ring; said process comprising:

(i) mixing compound of Formula (II)$_c$:

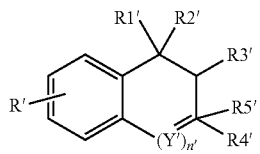

Formula (II)c wherein,
R1', or R3', or R5' are independently selected from the group consisting of hydrogen, alkoxy, unsubstituted or substituted phenyl, halogen, hydroxy, nitro, amino, carbonyl, —COOH, cyano, azo, unsubstituted or substituted benzyl group, C1 to C6 cyclo rings which optionally having one or more heteroatoms selected from N, O or S, heteroaryl, unsubstituted linear or branched alkyl having 2 to 10 C atoms, substituted linear or branched alkyl radical having 2 to 10 C atoms, in which one or more CH2 groups optionally each independently of one another be replaced by —C=O, —N—, —O—, —S—, —CH=CH—, or —C≡C—, unsubstituted linear or branched alkenyl radical having 2 to 10 C atoms, substituted linear or branched alkenyl radical having 2 to 10 C atoms; unsubstituted linear or branched alkynyl radical having 2 to 10 C atoms and substituted linear or branched alkynyl radical having 2 to 10 C atoms;

R2' is hydrogen;
R4' is none;
Y' is CR6', wherein R6' is selected from hydrogen, methyl, and phenyl;
R' is hydrogen or alkoxy; and
n' is 1, Formula (II)$_c$ forms six membered ring with powdered Oxone (H$_3$K$_5$S$_4$O$_{18}$) and sodium bicarbonate (NaHCO$_3$) in a ratio in a range of 2:3 in a mixture of acetone, ethyl acetate, and water to obtain a reaction mixture;

(ii) stirring the reaction mixture obtained in step (i) at room temperature in a range of 25 to 30° C. for a period in a range of 2-5 hours; and (iii) evaporating excess acetone under reduced pressure after completion of reaction, portioning the remaining reaction mixture between water and ethyl acetate and followed by purification to obtain compound of Formula I.

6. The process of claim 5, wherein the mixture of acetone, ethyl acetate, and water is in a ratio of 5:1:1.

7. The process of claim 5, wherein the compound of Formula I is selected from the group consisting of:
(i) 2,2,9b-Trimethyl-3a,4,5,9b-tetrahydronaphtho[2,1-d][1,3]dioxole (2o);
(ii) 7-Methoxy-2,2,9b-trimethyl-3a,4,5,9b-tetrahydronaphtho[1,2-d][1,3]dioxole (2p);
(iii) 2,2-Dimethyl-9b-phenyl-3a,4,5,9btetrahydronaphtho[2,1-d][1,3]dioxole (2q); and
(iv) 7-Methoxy-2,2-dimethyl-9b-phenyl-3a,4,5,9b-tetrahydronaphtho[1,2-d][1,3] dioxole (2r).

8. A simple, one step, stereospecific, oxone-acetone mediated, metal free process for preparation of a compound of Formula (IV),

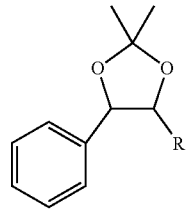

Formula (IV)

wherein R is selected from aryl and benzyl, said process comprising:
(i) mixing a compound of Formula (III):

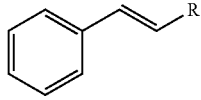

Formula (III)

with powdered Oxone (H$_3$K$_5$S$_4$O$_{18}$) and sodium bicarbonate (NaHCO$_3$) in a ratio in a range of 2:3 in a mixture of acetone, ethyl acetate, and water to obtain a reaction mixture;

(ii) stirring the reaction mixture obtained in step (i) at room temperature in a range of 25 to 30° C. for a period in a range of 2-5 hours; and (iii) evaporating excess acetone under reduced pressure after completion of reaction, portioning the remaining reaction mixture between water and ethyl acetate, and followed by purification to obtain the compound of Formula (IV).

9. The process of claim 8, wherein the mixture of acetone, ethyl acetate, and water is in a ratio of 5:1:1.

10. The process of claim 8, wherein the compound of Formula IV is selected from the group consisting of:
(i) (4S,5S)-2,2-Dimethyl-4,5-diphenyl-1,3-dioxolane (9a); and
(ii) (4S,5R)-2,2-Dimethyl-4,5-diphenyl-1,3— dioxolane (9b).

* * * * *